US012714735B2

(12) United States Patent
Bhardwaj

(10) Patent No.: US 12,714,735 B2
(45) Date of Patent: Aug. 25, 2026

(54) HERBAL COMPOSITION FOR CANCER

(71) Applicant: Samaara Bhardwaj, Delhi (IN)

(72) Inventor: Samaara Bhardwaj, Delhi (IN)

(73) Assignee: Sarnaara Bhardwaj, Delhi (IN)

( * ) Notice: Subject to any disclaimer, the term of this patent is extended or adjusted under 35 U.S.C. 154(b) by 289 days.

(21) Appl. No.: 18/596,984

(22) Filed: Mar. 6, 2024

(65) Prior Publication Data

US 2024/0207348 A1 Jun. 27, 2024

(51) Int. Cl.

| | |
|---|---|
| ***A61K 36/00*** | (2006.01) |
| ***A61K 31/4525*** | (2006.01) |
| ***A61K 36/53*** | (2006.01) |
| ***A61K 36/81*** | (2006.01) |
| ***A61K 36/82*** | (2006.01) |
| ***A61K 36/88*** | (2006.01) |
| ***A61K 36/899*** | (2006.01) |
| ***A61K 36/9066*** | (2006.01) |
| ***A61K 36/9068*** | (2006.01) |
| ***A61K 38/16*** | (2006.01) |

(52) U.S. Cl.
CPC .......... *A61K 36/82* (2013.01); *A61K 31/4525* (2013.01); *A61K 36/53* (2013.01); *A61K 36/81* (2013.01); *A61K 36/88* (2013.01); *A61K 36/899* (2013.01); *A61K 36/9066* (2013.01); *A61K 36/9068* (2013.01); *A61K 38/168* (2013.01)

(58) Field of Classification Search
CPC ...................................................... A61K 36/67
See application file for complete search history.

(56) References Cited

U.S. PATENT DOCUMENTS

2018/0125980 A1* 5/2018 Finley .................. A61K 31/352

* cited by examiner

*Primary Examiner* — Qiuwen Mi
(74) *Attorney, Agent, or Firm* — Davé Law Group LLC; Raj S. Davé

(57) ABSTRACT

Embodiments of the invention provide a herbal composition that may be utilized to case suffering, to improve quality of life, and to relieve the symptoms of patients suffering from chronic diseases with reduced side effects.

13 Claims, 12 Drawing Sheets

HERBAL COMPOSITION FOR CANCER

FIELD OF THE INVENTION

This invention relates to an herbal composition for treating cancer. In an embodiment, the invention is more particularly concerned with an herbal composition for lung cancer.

BACKGROUND OF INVENTION

Spices are important and a prevalent part of many cuisines. Spices usually come from woody shrubs, vines, trees, aromatic lichens and roots, flowers seeds, and fruits of herbaceous plants. They have unique flavors that come from the compounds present in them.

Out of 188 species in the dictionary 152 species linked them to 848 unique disease specific MeSH. There is an exponential increase in the therapeutic benefits associated with spices after more and more research is being conducted on the efficacy of spices over a wide range of diseases, especially the ones that have matched in the database to a specific disease. The top disease categories which were negatively associated with spices were vascular diseases, skin diseases, hypersensitivity and respiratory hypersensitivity. There were positive relations between spices and most viral diseases. The beneficial aspects of spices are due to the presence of bioactive phytochemicals such as polyphenols.

Spices have antimicrobial properties and can inhibit the growth of some microorganisms before they can produce toxins which will reduce diseases like food poisoning. Typically spices inhibit 75 of the bacterial species. There is a speculation that cooking the spices may inhibit the antimicrobial effects and cooking may destroy the potency of phytochemicals.

Spices also vary with climate. A greater proportion of bacteria is inhibited by receipt from hot climates than cool climates. Cooler climates contain less potent spices than cuisines from lower latitudes and elevations. There is a limit to how much of any one spice can be added before beneficial phytochemicals become phytotoxins. These spices and herbs have also been discovered to have medicinal properties. Most of the herbs and spices have a bio-active component which is being investigated for potential disease prevention and treatment. These herbs are spiced and are considered safe by the FDA. Herbs and spices also potentially have antimicrobial and antifungal activity. Some cuisines like Latin American and Chinese are becoming increasingly popular as people are becoming more health conscious as these cuisines have very low-fat levels. Herbs and spices are also antioxidants which are important to maintain the cell membrane integrity, proteins, nucleic acids. Imbalance can cause cell death, low immunity and even cancer. Herbs and spices also reduce inflammation which reduces cancer as 15% of inflammations lead to cancer.

Cancer is a large, heterogeneous class of diseases in which a group of cells display uncontrolled growth and invasion that intrudes upon and destroys adjacent tissues. Cancer often metastasizes, spreading to other locations in the body via the lymphatic system or through the bloodstream. According to the American Cancer Society, cancer is the second leading cause of death in the U.S., with half of all men and one-third of all women developing some form of cancer during their lifetimes (Snowden, ACS Researchers: Progress, Challenges in the War on Cancer, 2010, www.cancer.org/Cancer/news/News/acs-researchers-progress-chal). WHO accounted for over 7.6 million deaths and 12.7 million incidents of cancer globally in 2008 and estimates 21 million new cases by 2030 with a mortality rate of 13 million deaths per year (WHO Cancer Fact Sheet, February, 2011).

There is no total and complete cure for chronic diseases such as cancer. The limited numbers of drugs developed to treat cancer, suffer from one or more disadvantages, most notably adverse side-effects, complex administration methods, and often high cost. Cancer treatment methods, including chemotherapy, radiation therapy, and surgery often possess significant adverse side effects. These generally include removal of healthy tissue during surgery, death of non-cancerous cells during chemotherapy and radiation therapy, and significant reduction of white blood cells and other immune system components leading to increased susceptibility for infection. Moreover, the toxicity of many cancer treatments can cause the failure of organ systems, such as the liver and the kidney, as a complication of those treatments.

Therefore, there remains a need for simple and effective natural compositions that are well tolerated, simple to administer, and relatively inexpensive to relieve the symptoms of chronic diseases such as cancer.

SUMMARY OF THE INVENTION

An embodiment of the invention provides an herbal composition that could be utilized to case suffering, to improve quality of life, and to relieve the symptoms of patients suffering from chronic diseases with reduced side effects.

In an embodiment, product comprising a composition having an extract of an herbal spice comprising green tea, piperine and turmeric, wherein the composition has IC50 value for cytotoxicity less than or equal to about 10 μg/ml and the extract is extracted using an organic solvent comprising DMSO.

In an embodiment, the extract is a purified extract.

In an embodiment, the extract has an extraction yield of about 80% w/w to 99% w/w.

In an embodiment, the composition provides a dose dependent cytotoxicity.

In an embodiment, the composition further comprises ginger.

In an embodiment, the composition further comprises ashwagandha.

In an embodiment, the composition further comprises garlic

In an embodiment, the composition further comprises Tulsi.

In an embodiment, the composition further comprises wheat grass.

In an embodiment, the composition is configured to inhibit a cancer.

In an embodiment, the cancer comprises lung cancer.

In an embodiment, the weight ratio of the extract of green tea, piperine and turmeric are equal in the composition.

In an embodiment, wherein in the composition the weight ratio of the extract of turmeric is about double compared to extracts of other herbal components.

In an embodiment, the composition provides a dose-independent cytotoxicity.

In an embodiment, the composition is in the form of powder.

In an embodiment, the composition is a liquid composition.

In an embodiment, the composition is a semi-solid composition or paste form.

In an embodiment, the composition is a water-soluble composition.

In an embodiment, the composition comprises a soluble protein.

In an embodiment, the soluble protein comprises turmerin.

In an embodiment, the composition is configured to treat a disease in a subject.

In an embodiment, the disease is a cancer.

In an embodiment, the subject is a mammal.

In an embodiment, IC50 value is about 1 μg/ml to about 10 μg/ml.

In an embodiment, IC50 value is about 2 μg/ml to about 6 μg/ml.

In an embodiment, the composition has inhibition percentage more than 75% and less than 95% as tested on human Lung cancer cell line (A549) using MTT assay.

In an embodiment, the composition has inhibition percentage more than 85% and less than 95% as tested on human Lung cancer cell line (A549) using MTT assay.

In an embodiment, the composition is configured to increase an enzyme activity selected from the group consisting of superoxide dismutase and catalase.

In an embodiment, the composition comprises an excipient.

In an embodiment, the composition is in an oral dosage form.

In an embodiment, the oral dosage form is either tablet or capsule.

In an embodiment, the composition comprises an emulsifier.

In an embodiment, the composition has a half-life stability of about 1 to 5 years at a room temperature.

In an embodiment, the composition has a half-life stability of about 3 years at a room temperature.

In an embodiment, method of treatment comprising taking a product of claim 1 and administering into the subject, wherein the composition is configured to treat a cancer comprising a lung cancer.

In an embodiment, product comprising a formulation comprising particles of a mixture of herbs comprising at least three components selected from piperine, Ginger, Garlic, Tulsi, Wheatgrass, Ashwagandha, turmeric; wherein the particles are coated with an emulsifier and a lipophilic solvent, such that the formulation is water-soluble.

In an embodiment, the formulation further comprises pharmaceutically acceptable excipients.

In an embodiment, the particles are in a size range of about 50 nm to 500 nm.

In an embodiment, the particles are in a range of about 200 nm to about 400 nm.

In an embodiment, the product is a functional health food.

In an embodiment, the emulsifier is in amount of 30 to 45 w/w %. Emulsifier is in amount of 35 w/w %, 40 w/w %, 45 w/w %, 50 w/w %, 60 w/w %, 70 w/w % of the composition.

In an embodiment, the lipophilic solvent in amount of 5 to 70 w/w %. Lipophilic solvent is in amount of 35 w/w %, 40 w/w %, 45 w/w %, 50 w/w %, 60 w/w %, 70 w/w % of the composition.

In an embodiment, particles in amount of about 1 to 20 w/w %. Particles is in amount of 5 w/w %, 10 w/w %, 15 w/w %, 20 w/w %, 30 w/w %, 40 w/w % of the composition.

In an embodiment, pH of the formulation is about 6.5 to 7.5.

In an embodiment, the product has a shelf-life of about 3 years at a room temperature.

In an embodiment, the composition is diluted in a ratio of about 1:10 to 1:200.

In an embodiment, the product is configured to treat a disease.

In an embodiment, the disease is a cancer.

In an embodiment, the cancer is a lung cancer.

In an embodiment, the composition is free of a pH buffer.

In an embodiment, method comprising extracting extract from a herb comprising green tea, piperine and turmeric; mixing extracts from all herbs in equal ratio; and adding emulsifier to prepare to a water-soluble composition.

In an embodiment, the extract is purified.

In an embodiment, the extraction has an extraction yield of about 90% w/w to about 99 w/w %.

In an embodiment, the water-soluble composition has IC50 approximately same as Doxorubicin.

In an embodiment, the composition has IC50 approximately same as Doxorubicin.

BRIEF DESCRIPTION OF THE FIGURES

The accompanying drawings, which are included to provide further understanding of the present invention disclosed in the present disclosure and are incorporated in and constitute a part of this specification, illustrate aspects of the present invention and together with the description serve to explain the principles of the present invention. In the drawings.

DETAILED DESCRIPTION

Figure 1:
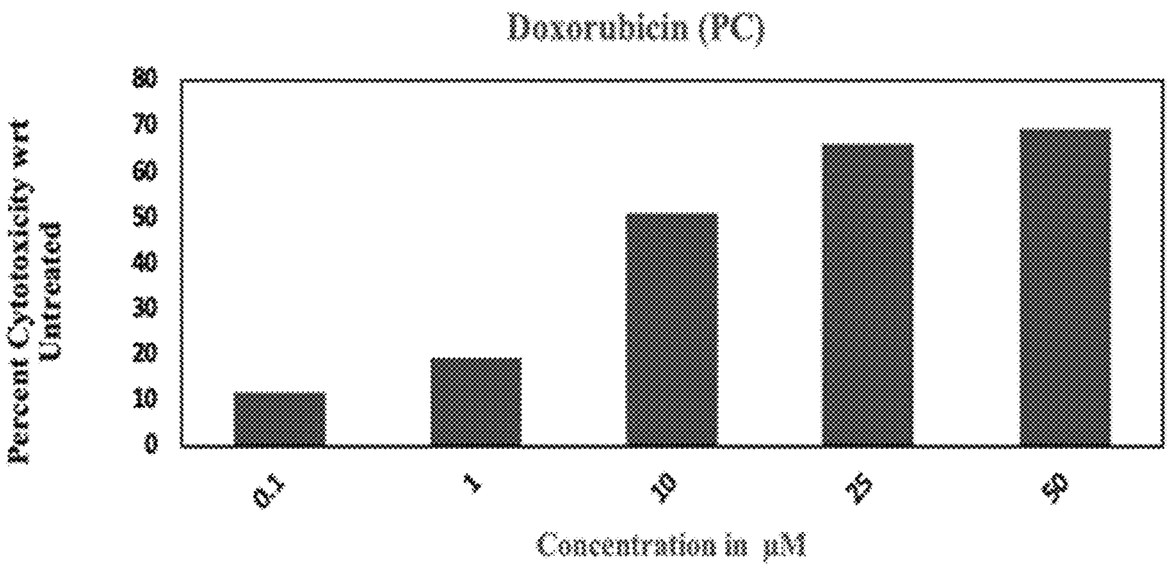
FIG. 1 shows cytotoxicity assay of Doxorubicin.
Figure 2:
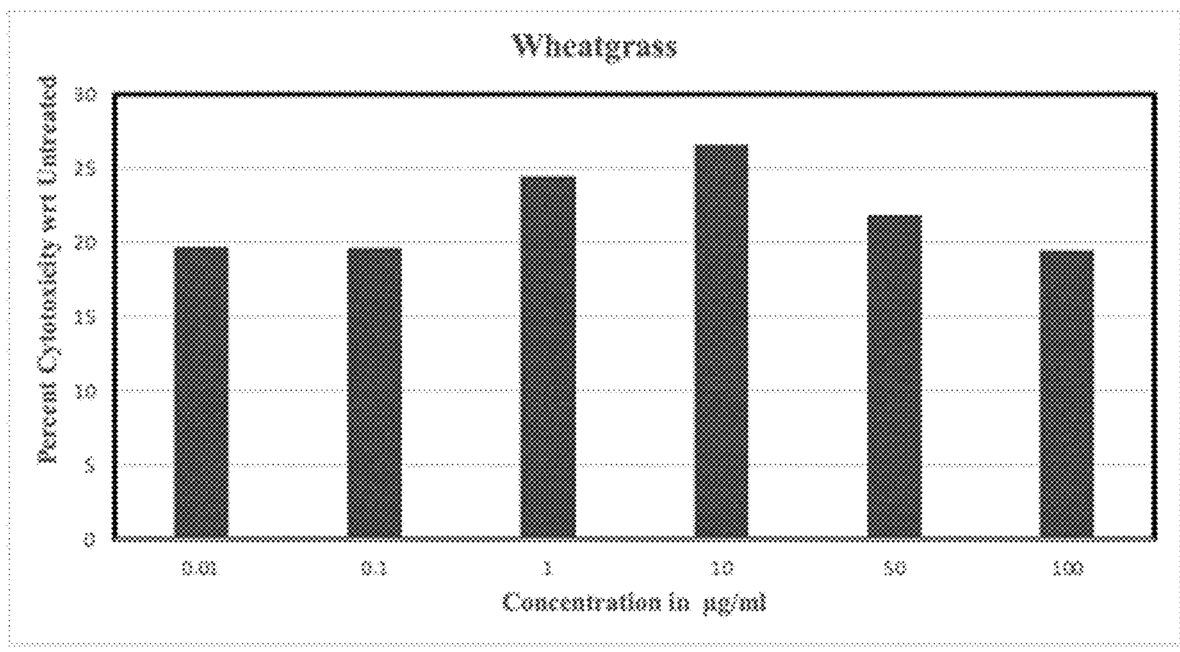
FIG. 2 shows cytotoxicity assay of wheatgrass.
Figure 3:
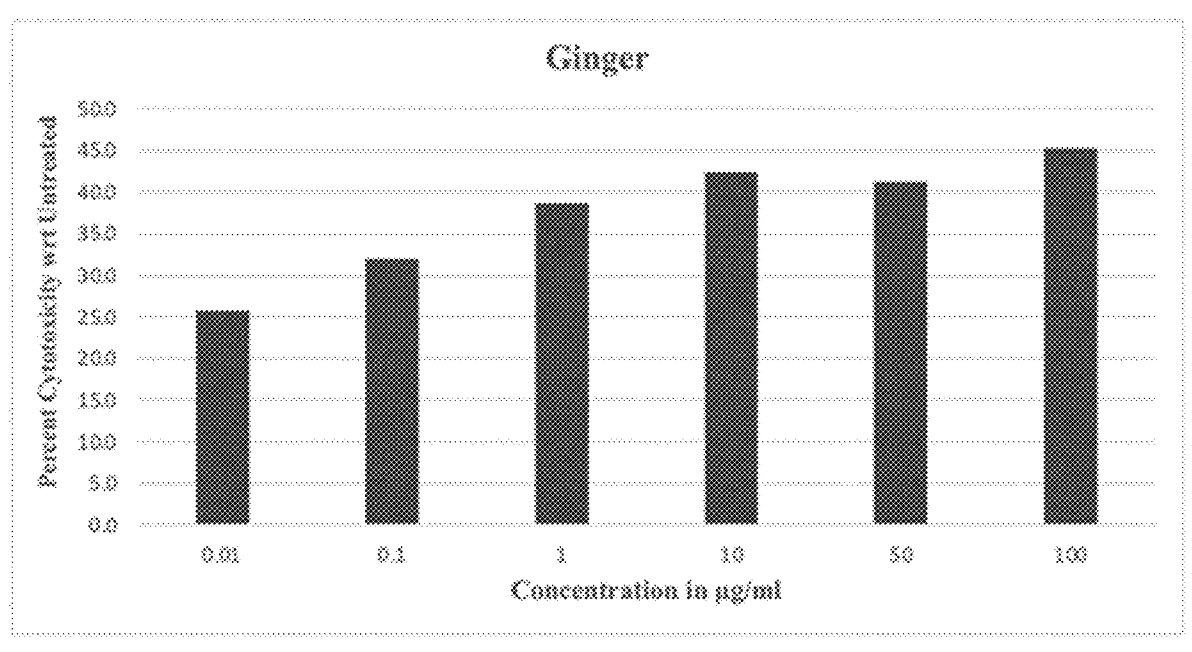
FIG. 3 shows cytotoxicity assay of ginger.
Figure 4:
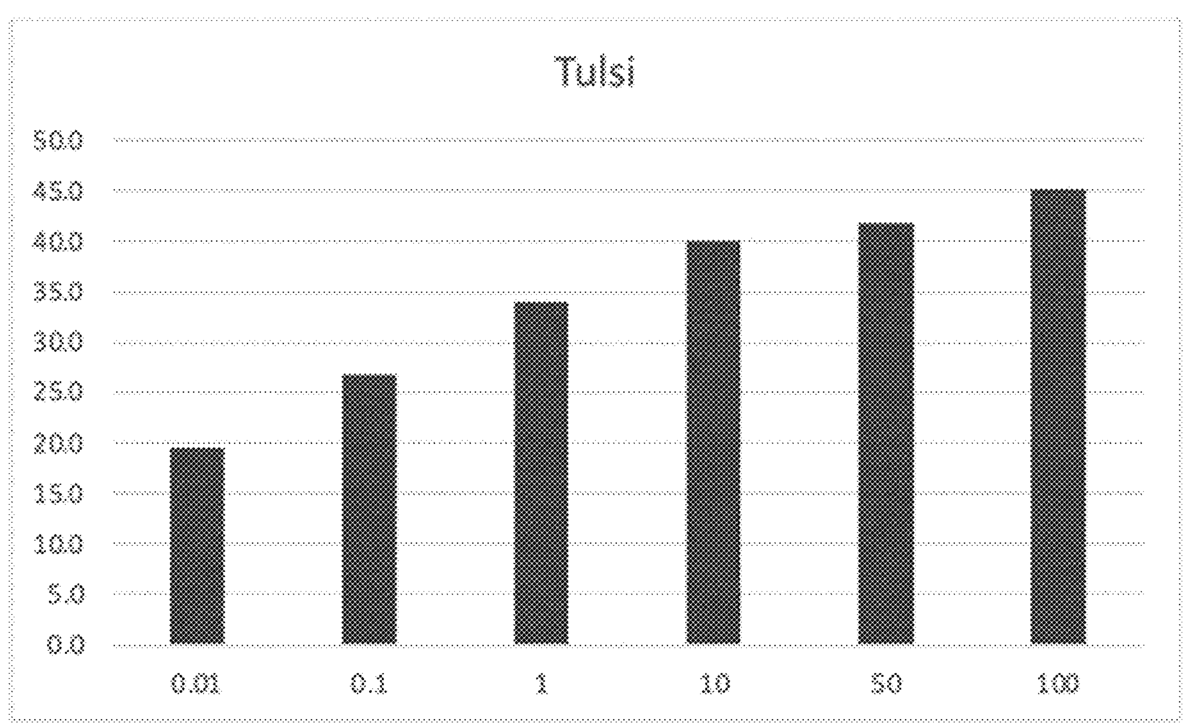
FIG. 4 shows cytotoxicity assay of tulsi.
Figure 5:
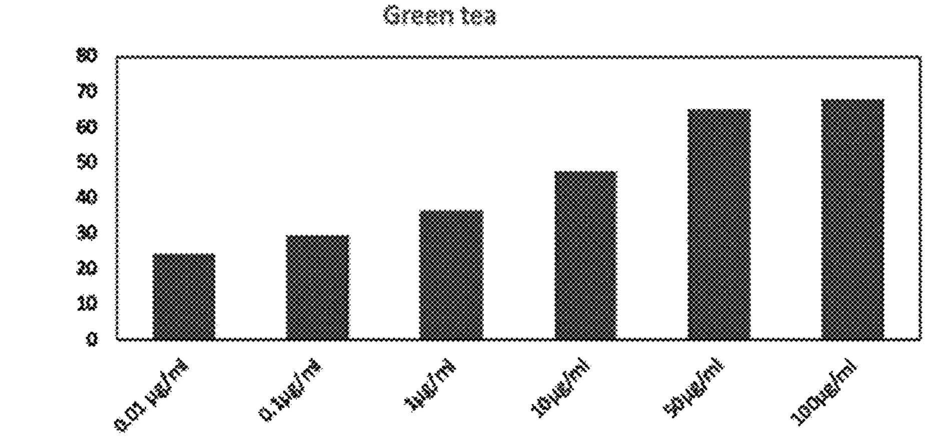
FIG. 5 shows cytotoxicity assay of green tea.
Figure 6:
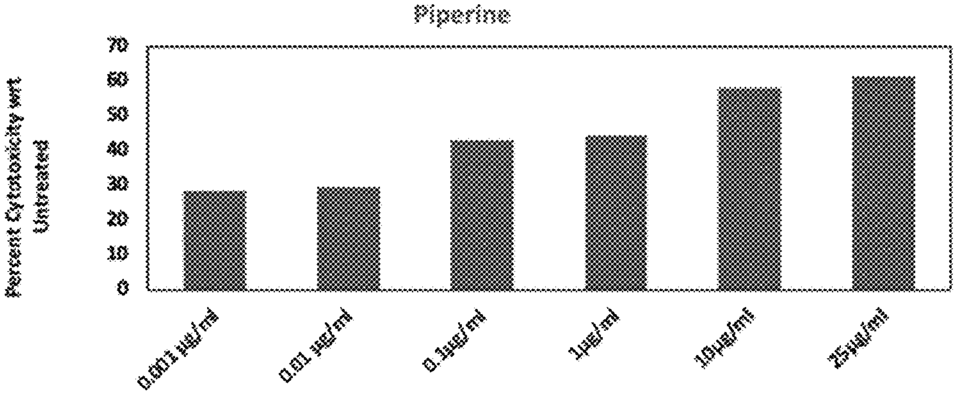
FIG. 6 shows cytotoxicity assay of piperine.
Figure 7:
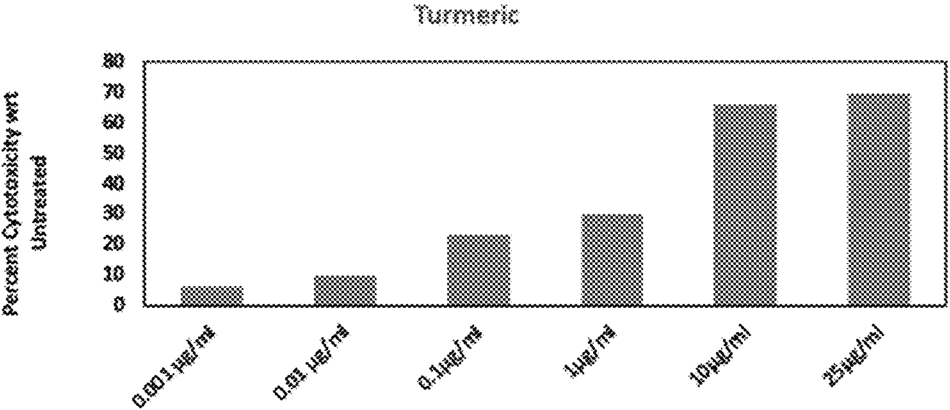
FIG. 7 shows cytotoxicity assay of turmeric.
Figure 8:
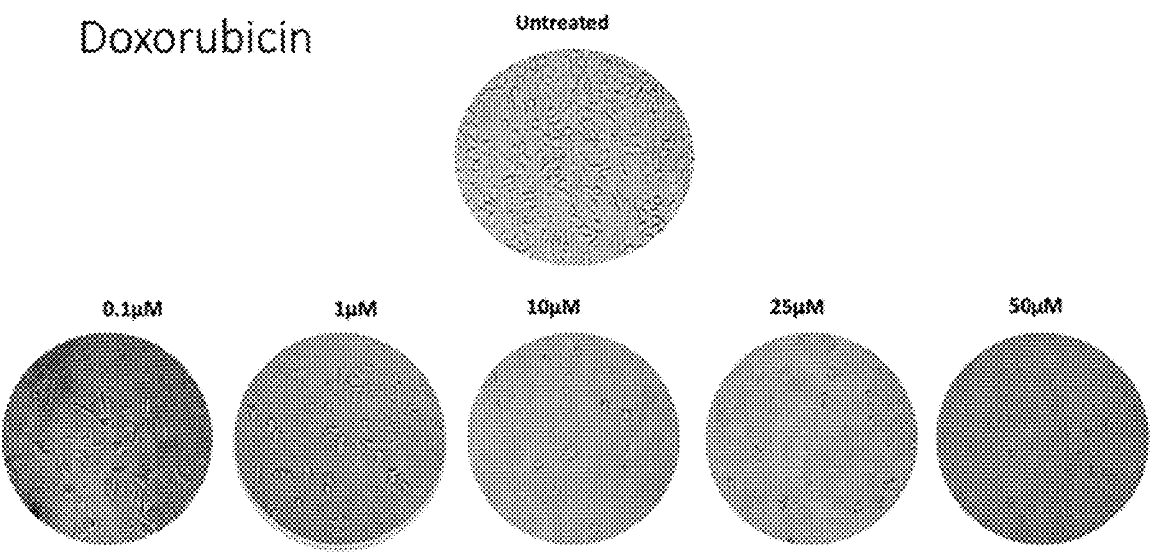
FIG. 8 shows in-vitro cytotoxic potential of Doxorubicin in human Lung cancer cell line (A549) by antioxidant assay.
Figure 9:
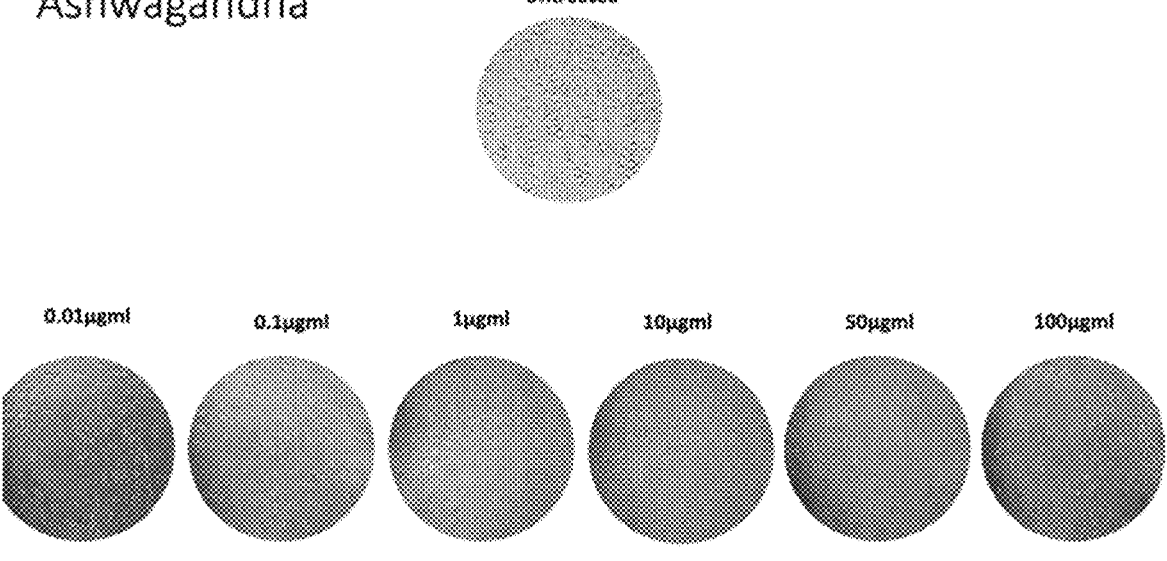
FIG. 9 shows in-vitro cytotoxic potential of Ashwagandha in human Lung cancer cell line (A549) by antioxidant assay.
Figure 10:
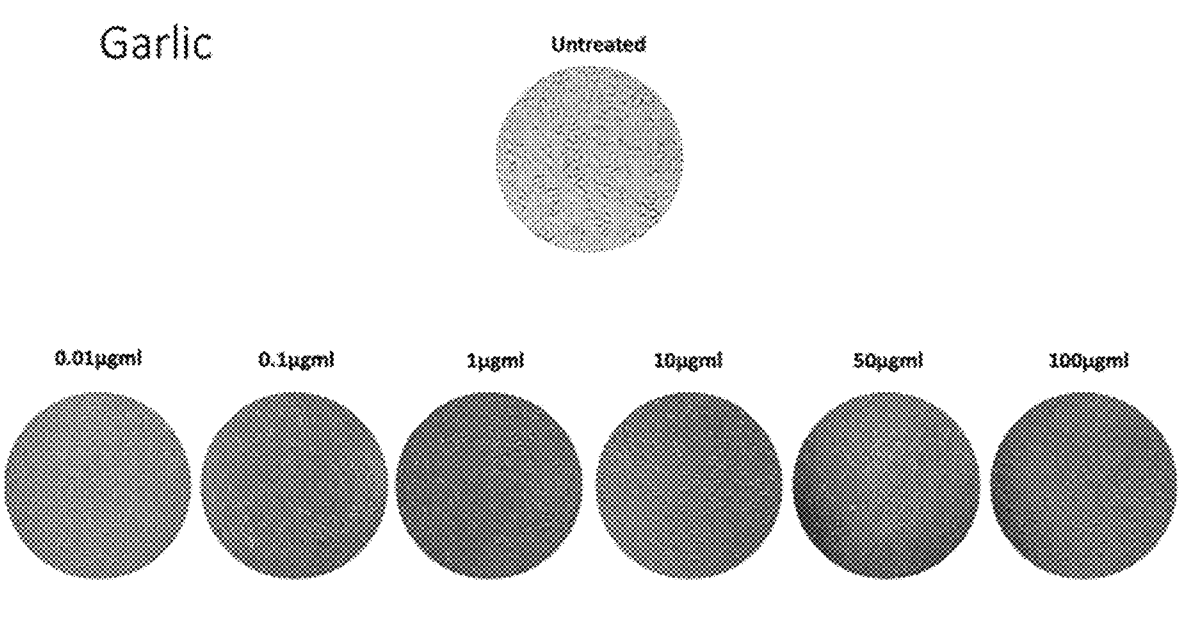
FIG. 10 shows in-vitro cytotoxic potential of garlic in human Lung cancer cell line (A549) by antioxidant assay.
Figure 11:
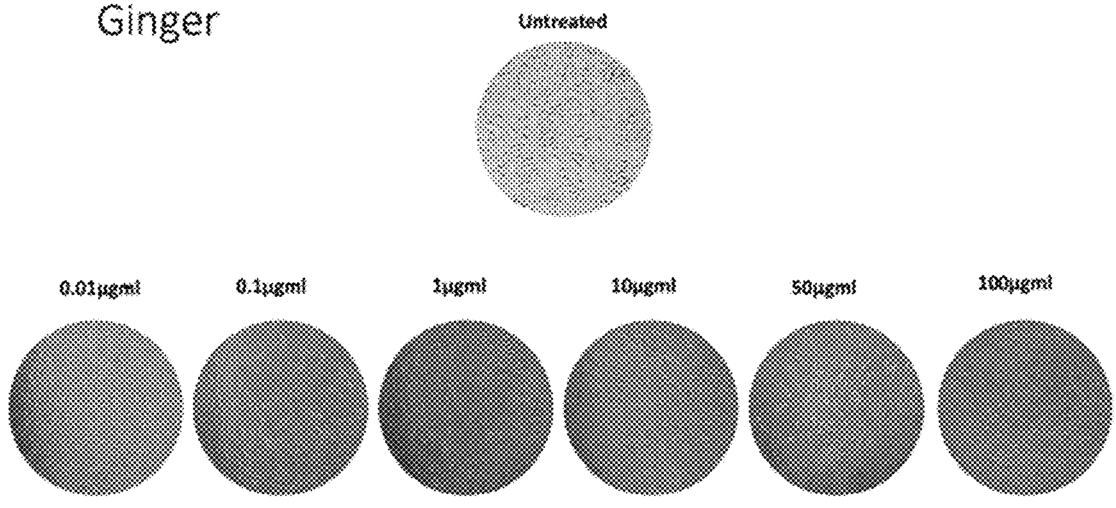
FIG. 11 shows in-vitro cytotoxic potential of ginger in human Lung cancer cell line (A549) by antioxidant assay.
Figure 12:
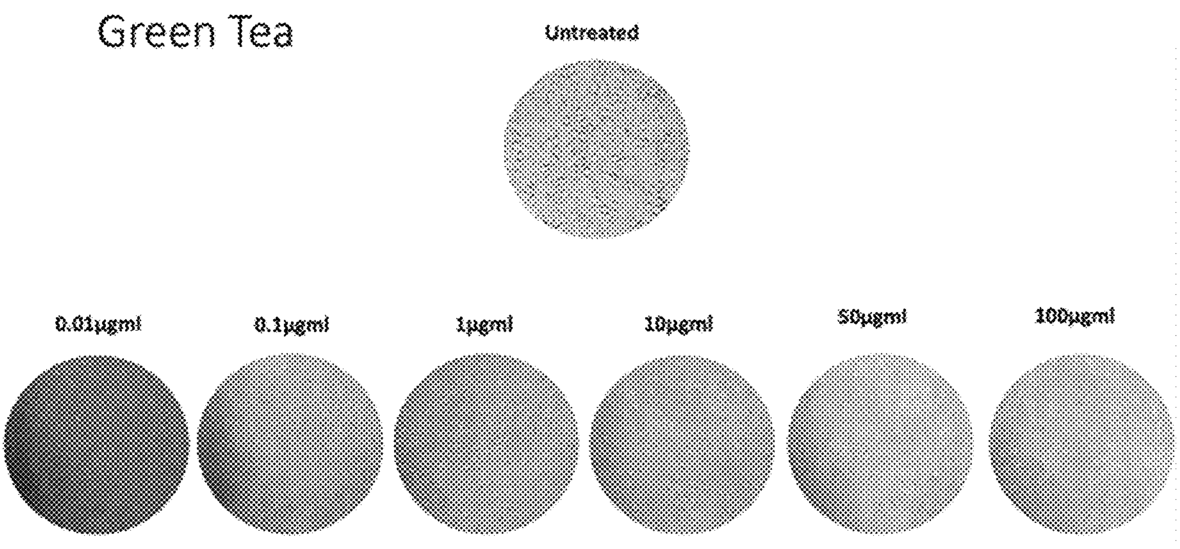
FIG. 12 shows in-vitro cytotoxic potential of green tea in human Lung cancer cell line (A549) by antioxidant assay.
Figure 13:
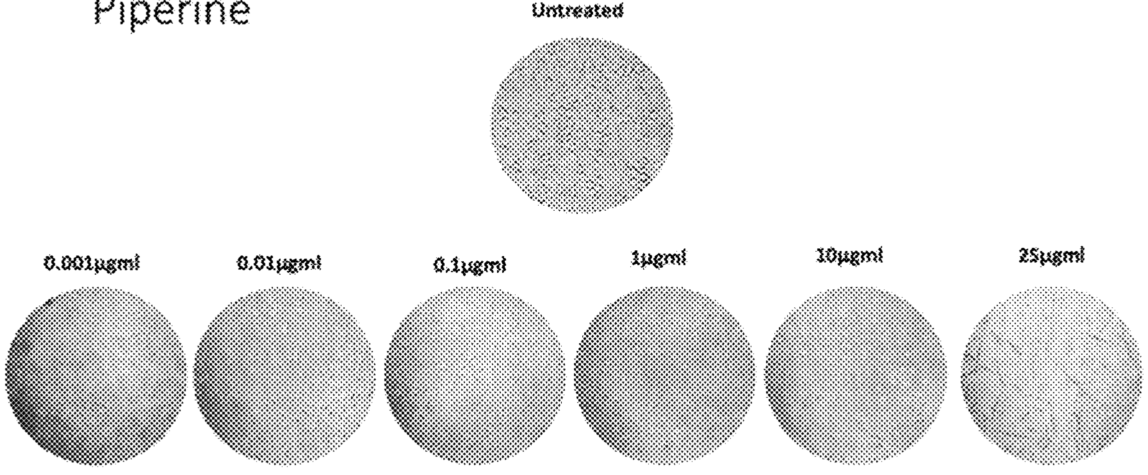
FIG. 13 shows in-vitro cytotoxic potential of piperine in human Lung cancer cell line (A549) by antioxidant assay.
Figure 14:
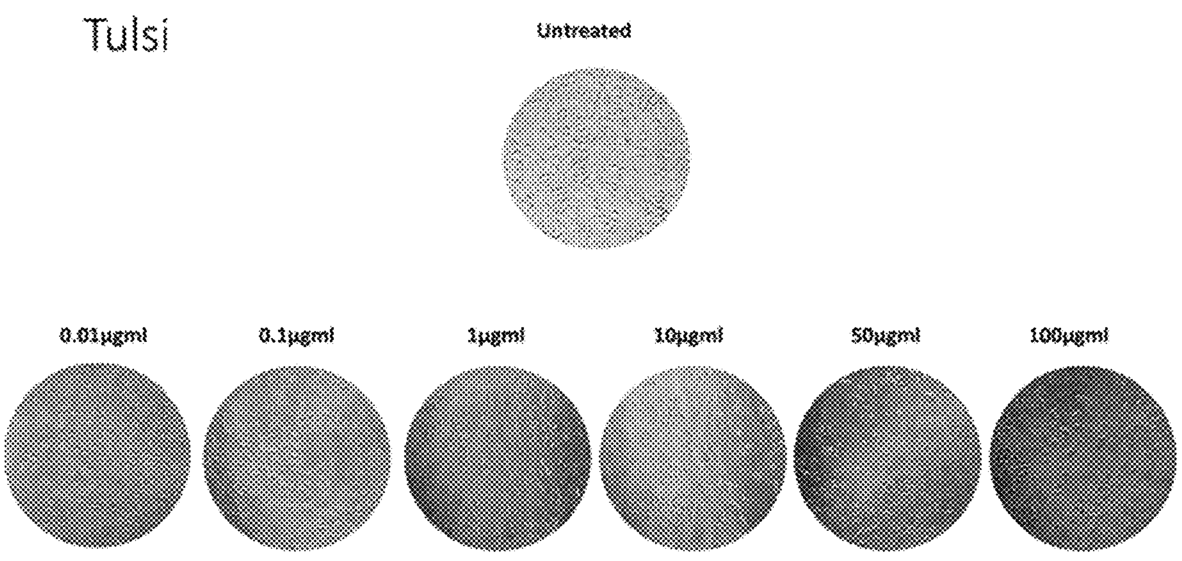
FIG. 14 shows in-vitro cytotoxic potential of tulsi in human Lung cancer cell line (A549) by antioxidant assay.
Figure 15:
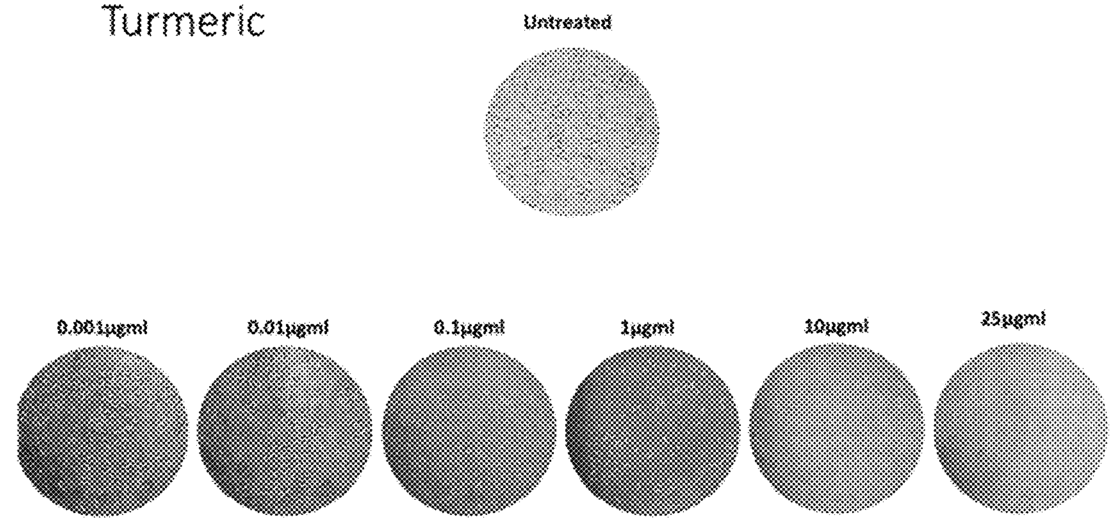
FIG. 15 shows in-vitro cytotoxic potential of turmeric in human Lung cancer cell line (A549) by antioxidant assay.
Figure 16:
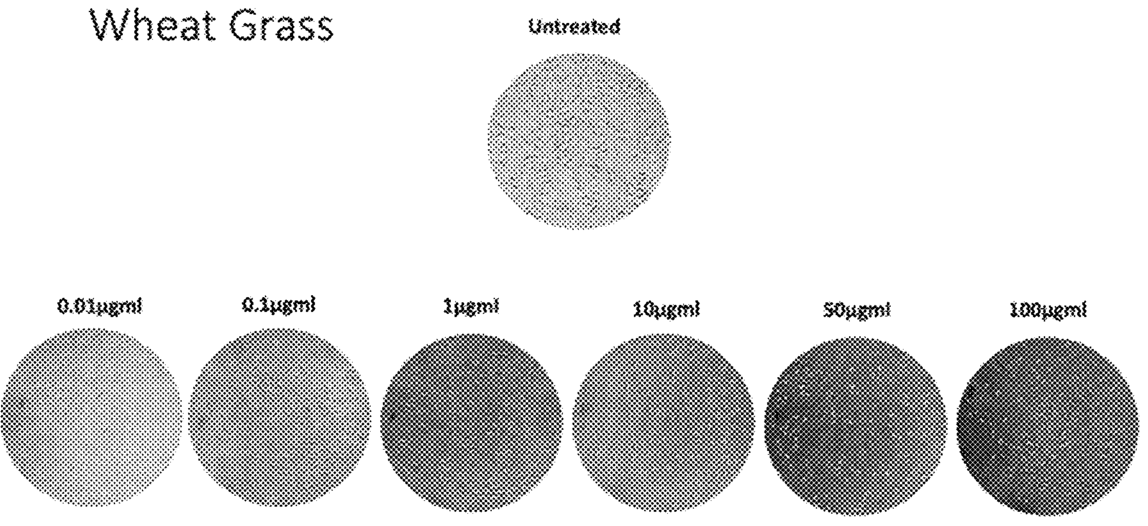
FIG. 16 shows in-vitro cytotoxic potential of wheat grass in human Lung cancer cell line (A549) by antioxidant assay.
Figure 17:
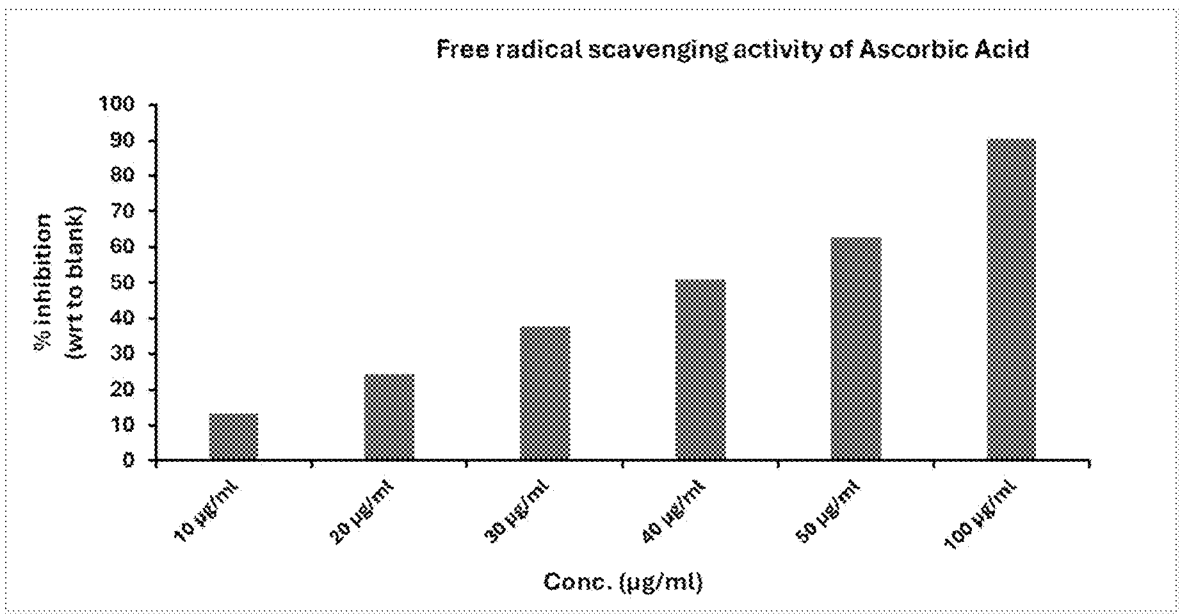
FIG. 17 shows free radical scavenging activity of ascorbic acid.
Figure 18:
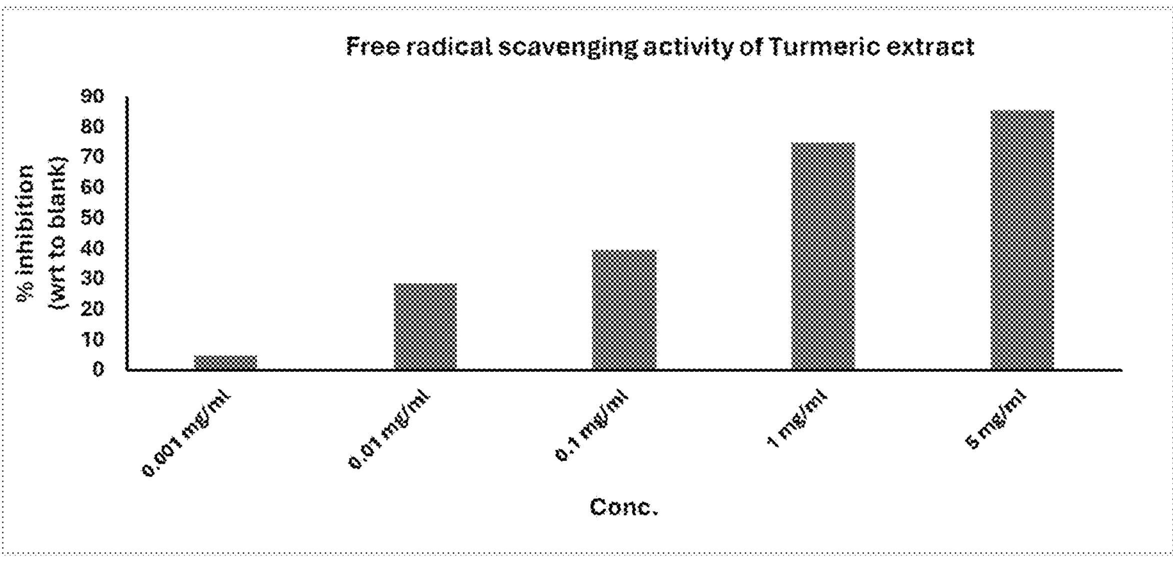
FIG. 18 shows free radical scavenging activity of turmeric extract.
Figure 19:
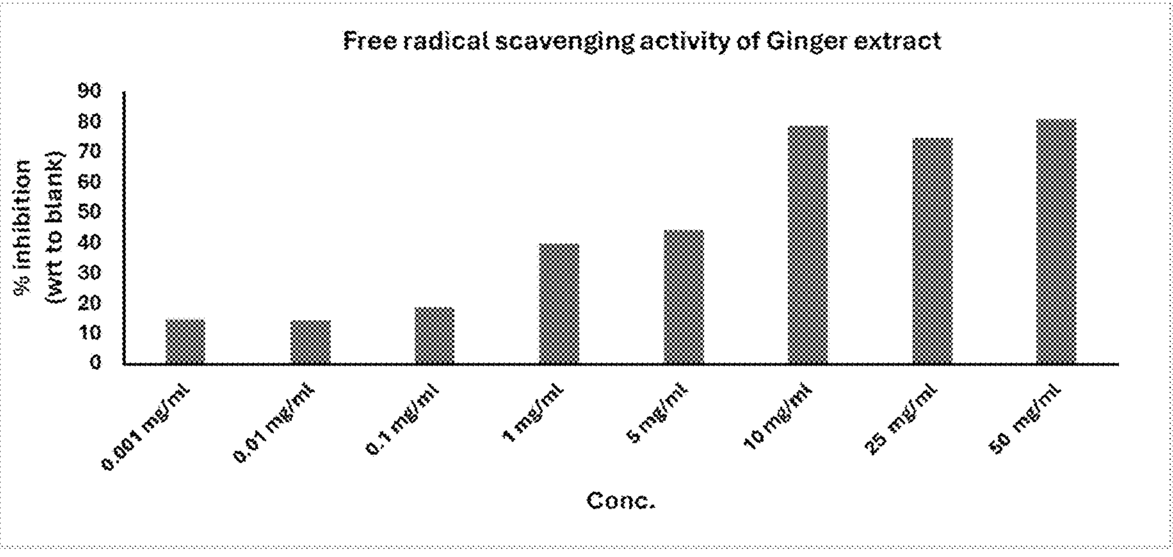
FIG. 19 shows free radical scavenging activity of ginger extract.
Figure 20:
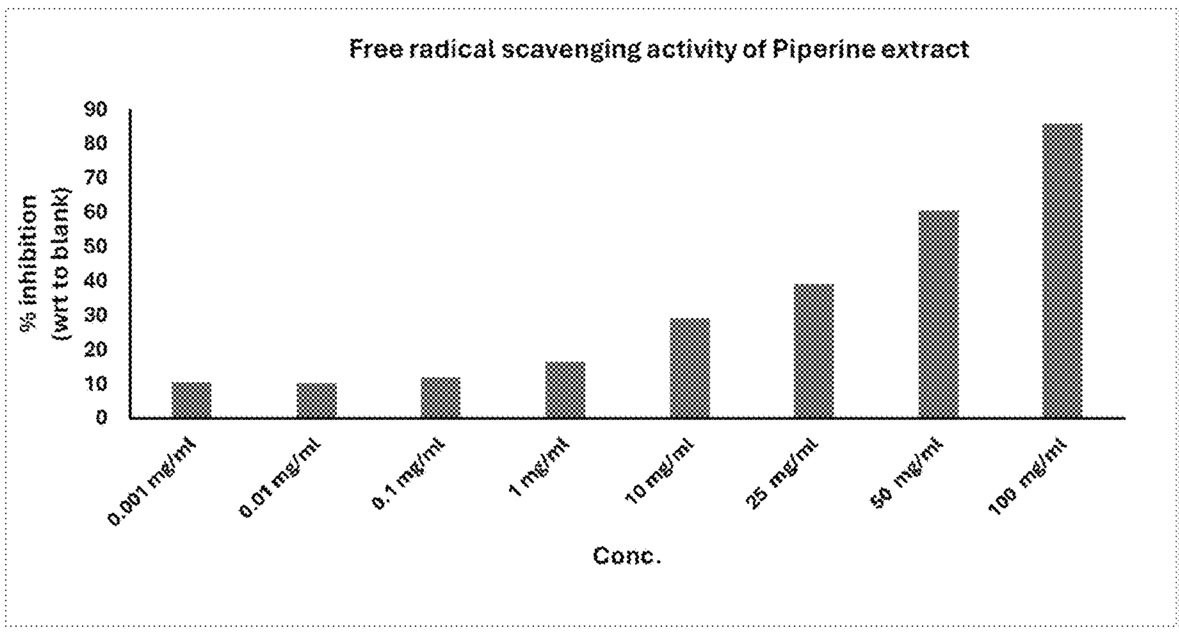
FIG. 20 shows free radical scavenging activity of piperine extract.
Figure 21:
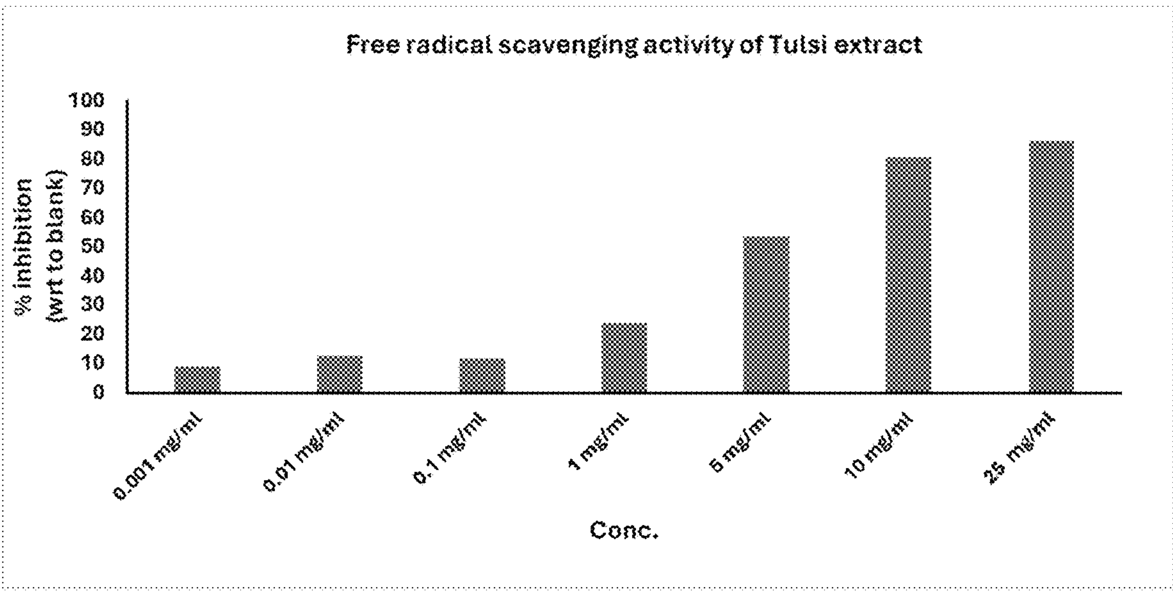
FIG. 21 shows free radical scavenging activity of tulsi extract.
Figure 22:
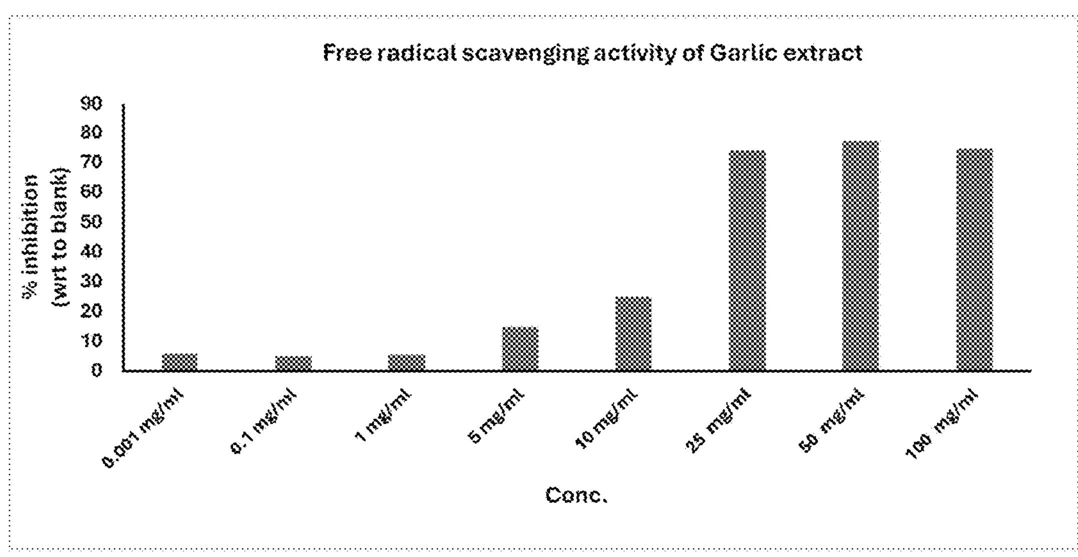
FIG. 22 shows free radical scavenging activity of garlic extract.
Figure 23:
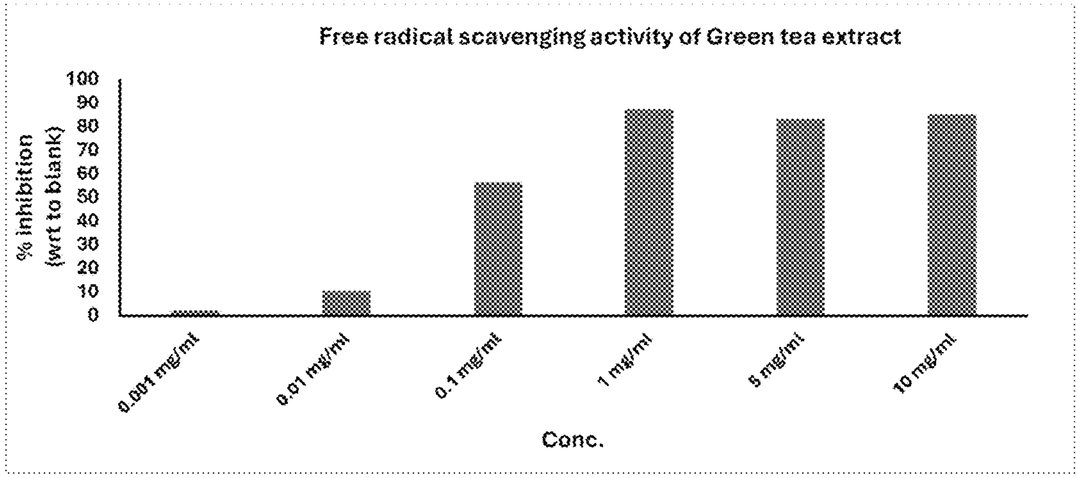
FIG. 23 shows free radical scavenging activity of green tea extract.
Figure 24:
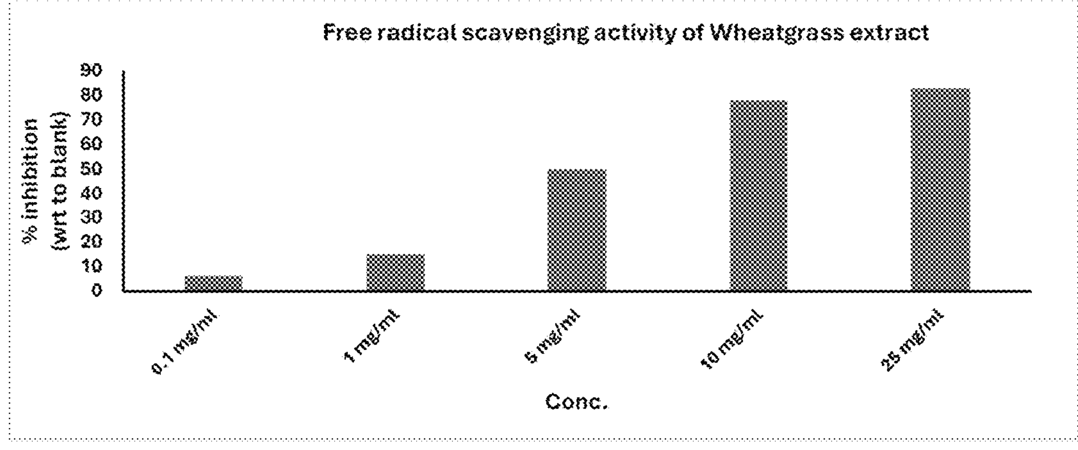
FIG. 24 shows free radical scavenging activity of wheat grass extract.
Figure 25:
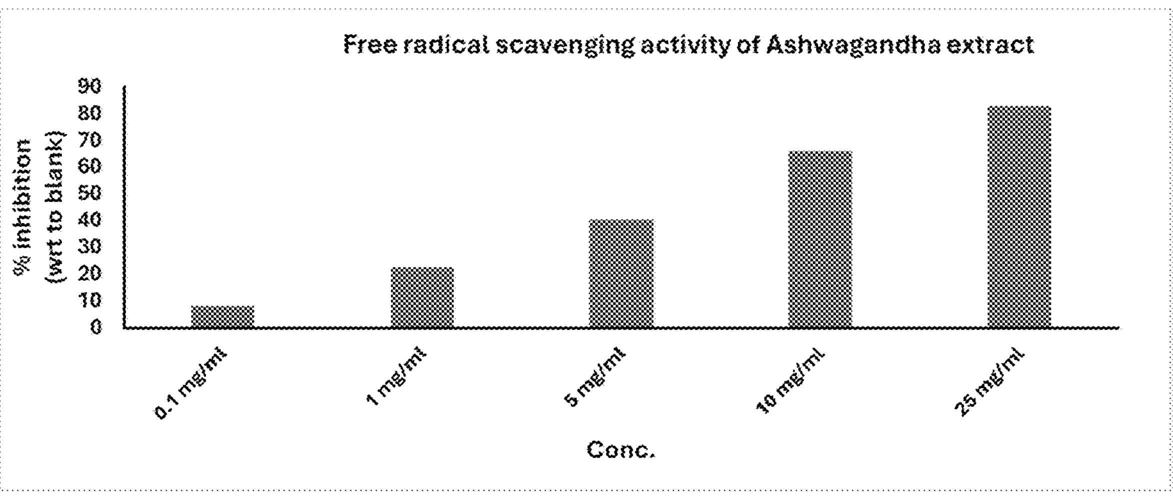
FIG. 25 shows free radical scavenging activity of ashwagandha extract.
Figure 26:
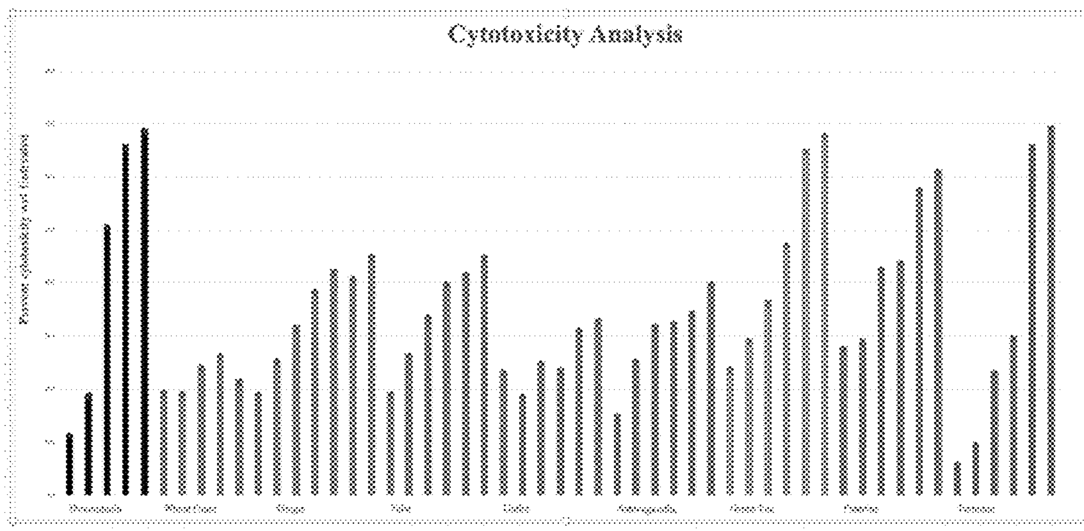
FIG. 26 shows graphical analysis of Increasing concentration of Spices showed increased cytotoxicity in human lung carcinoma epithelial cell line. Bar graph showing increased cytotoxicity with increasing concentration of spices.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denotes the same elements.

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); PCR: The Polymerase Chain Reaction, (Mullis et al., eds., 1994); Harlow and Lane (1988) Antibodies, A Laboratory Manual, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000), and *Handbook of Experimental Immunology,* 4th edition (D. M. Weir & C. C. Blackwell, eds., Blackwell Science Inc., 1987).

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items, and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Unless otherwise defined herein, scientific and technical terms used in connection with the present invention shall have meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

The recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C", and "A, B, and/or C" means A alone, B alone, C alone, A and B together, A and C together, B and C together, or A, B and C together.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The present invention is directed towards multiple embodiments. The following disclosure is provided to enable a person having ordinary skill in art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications, and equivalents consistent with the principles and features disclosed. For purposes of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

Definitions

As used herein, "extract" refers to an herb extract that may be prepared by liquid or powder extraction or any other method known to one having skill in the art, and may or may not include a step of concentrating the extract as well as further processing (for example, but not limited to, drying and/or refluxing). The extractions disclosed herein may be obtained from any part of a plant (for example, but not limited to, roots, leaves, flowers, seeds, stems, rhizome) as well as whole plants.

As used herein, "crude extract" refers to the extract received from the raw material just after employing the extraction procedure. The extract may be containing many undesired materials. The crude extract is further subjected to purification and different fractionation steps to remove the undesired materials and purify the extract.

As used herein, "purified extract" or "pure extract" or similar refers to the extract that has undergone purification and different fractionation steps, such as physical methods such as filtration, distillation, crystallization, chromatography etc., chemical purification such as functionalization or other known methods.

As used herein, "treating" or preventing a disease, disorder, or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the disease or condition, even if the underlying pathophysiology is not affected, such as treating the pain of a subject by administration of an analgesic agent even though such agent does not treat the cause of the pain.

As used herein, "subject" is a mammal including a human. Mammals include, but are not limited to, farm animals, sport animals, pets, non-human primates, mice and rats. Individuals also include companion animals including, but not limited to, dogs and cats. In one aspect, an individual is a human. In another aspect, an individual is a rodent.

As used herein, "IC50" Half maximal inhibitory concentration (IC50) is a measure of the potency of a substance in inhibiting a specific biological or biochemical function. IC50 is a quantitative measure that indicates how much of a particular inhibitory substance (e.g. drug or herbal composition of the present invention) is needed to inhibit, in vitro, a given biological process or biological component by 50%. The biological component could be an enzyme, cell, cell receptor or microorganism.

As used herein, "Herb" or "herbal spice" or similar refers to a range of plants utilized for culinary and/or therapeutic applications. For example but not limited to Agarwood; Agarwood; Almond, Aloe Vera; Bitter; Amber Oil, Avocado, Fossilized; Amber Oil, Fossilized; Ambrette Seed Fine; Ambrette Seed; Amyris; Angelica Root; Angelica Seed; arborvitae; Armoise (Mugwort); Balsam of Peru Oil; Balsam of Peru Resin; Basil, Sweet ct Linalool; Basil, Sweet ct Linalool; Basil, Sweet ct Methyl Chavicol; Beeswax Absolute; Bergamot; Bergamot k; Bergamot; Bergamot; Black Cumin; Black Currant; Caraway; Cardamom; Carnation Absolute; Carnation Extract; Carrot Seed; Cassie Absolute; Cedarwood, Atlas; Cedarwood, Himalayan; Cedarwood, Texas; Cedarwood, Virginia; Celery Seed; Chamomile, Bluc; Chamomile, Roman; Champaca; Cilantro; Cinnamon; Cinnamon Bark; Cistus Traditional; Citronella; Citronella Wild; Clary Sage Absolute; Clary Sage, Bulgaria; Clary Sage, Russia; Clary Sage, USA; Clove Bud; Clove; Cocao Absolute; Coconut; Coffee Bean; Coffee Bean Oil; Cognac, Green; Coriander Seed; Coriander Seed; Cucumber Hydrosol; Cumin Seed; Cypress Leaf; Cypress, Blue; Davana; Eucalyptus, Bluc Gum; Eucalyptus, Blue Mallec; Eucalyptus, Lemon; Eucalyptus, Narrow Leaf; Eucalyptus, Narrow Leaf; Fennel, Sweet; Fennel, Sweet; Fenugreek; Fir Needle; Fir, Balsam; Fir, Balsam Absolute; Fir, Balsam Absolute; Fir, Douglas; Fir, Silver; Frankincense; Frankincense, Somalia; Frankincense Frercana; Frankincense, Oman; Frankincense, Oman Rare; Frankincense, Somalia; Galbanum; Geranium Absolute; Geranium, Egypt; Geranium, Rose; Geranium, South Africa; Ginger; Ginger; Ginger; Ginger Lily; Ginger, Fresh; Goji; Grapefruit, Pink; Grapefruit, Ruby Red; Grapefruit, White; Hay Absolute; Helichrysum, Albania; Helichrysum, Croatia; Hemp; Hyssop Decumbens; Immortelle Absolute; Jasmine Absolute, Egypt; Jasmine Absolute, Egypt; Jasminc Absolute; Jasmine Absolute; Jasmine; Jasmine Concrete; Jasmine Extract; Jasmine Sambac Absolute; Jasmine Sambac Absolute; Juniper Berry; Juniper Berry; Juniper Leaf/Berry, Nepal; Juniper Leaf/Branch; Kava Kava; Kava Kava; Labdanum Absolute, Clear; Laurel Leaf; Lavandin, Grosso; Lavender High Elevation; Lavender Wild; Lavender Absolute; Lavender Hydrosol; Lavender, Bulgaria; Lavender, France; Lavender, Maillette; Lemon; Lemon Tea Tree; Lemongrass; Lemongrass Wild; Lime Distilled; Lime Expressed; Lime Essence Oil; Lime, Distilled; Liquidambar (Styrax; Lotus Absolute, Pink; Lotus Absolute, White; Availability; Mandarin, Green; Mandarin, Red; Mandarin, Yellow; Mango'Marjoram; Melaleuca; Melissa; Myrrh; Myrrh, Somalia; Myrrh, Somalia; Myrtle, Green; Nagarmotha (Cypriol; Neroli Extra; Neroli Extra; Neroli, Egypt; Neroli, Egypt; Neroli, France; Neroli, France; Neroli, Morocco; Niaouli; Oakmoss Absolute; Orange Wild; Orange Blossom Absolute; Orange Blossom Absolute Fine; Orange Blossom Extract; Orange Essence Oil; Orange, Bitter Green; Orange, Bitter Red; Orange, Blood; Orange, Wild; Orange, Sweet; Oregano, Turkey; Orris Butter (15 irones; Osmanthus Absolute; Palmarosa, Nepal Wild; Palmarosa, Sri Lanka; Palo Santo; Patchouli Double Distilled; Patchouli; Patchouli, Dark; Patchouli, Light; Patchouli, Sri Lanka; Pepper, Black; Peppercorn, Pink; Peppermint, Chocolate; Peppermint, France; Peppermint; Peppermint, USA; Petitgrain Absolute; Petitgrain Bigarade; Petitgrain sur Fleurs; Petitgrain, Mandarin; Petitgrain, Mandarin; Piper, aduncum; Piper, malacophyllum; Pomegranate Seed; Ravensara Wild; Rhododendron Leaf; Rosalina; Rose Absolute, Bulgaria; Rose Absolute, Bulgaria; Rose Absolute, Egypt; Rose Absolute, Egypt; Rose Absolute, Morocco; Rose Absolute, Morocco; Rose de Mai Absolute; Rose de Mai Concrete; Rose de Mai Extract; Rose Hip Seed; Rose Otto, Bulgaria; Rosc Otto, Turkey; Rose Otto, White; Rosemary Antioxidant; Rosemary ct Cincole; Rosemary ct Cincole; Rosemary ct Verbenone; Sage; Sandalwood Rare; Sandalwood Absolute, New Caledonia; Sandalwood, Australian Premium; Sandalwood, New Caledonia; Sandalwood, New Caledonia Extra; Sandalwood, Royal Hawaiian; Sea Buckthorn; Seaweed Absolute; Spearmint; Spearmint, USA; Spikenard; Spikenard, Green Wild; Spruce, Black; St. John's Wort; Tagetes; Tamanu (Foraha Oil; Tangerine Murcott; Tansy, Blue; Tea Tree; Thyme ct Linalool; Tobacco Absolute; Tonka Bean Absolute; Tonka Bean Absolute 20; Tuberose Absolute; Tuberose Extract; Turmeric; Turmeric; Vanilla Absolute; Vanilla Bourbon; Vanilla Bourbon; Vanilla Bourbon; Verbena; Vetiver Double Distilled; Vetiver, El Salvador; Vernonia, polyanthes; Vetiver, Haiti; Vetiver, Sri Lanka; Violet Leaf Absolute; Violet Leaf Absolute; Virola, surinamensis; Vitamin E Oil; White Sage; Wintergreen Wild; Yarrow, Blue; Ylang Ylang Absolute; Ylang Ylang Complete, Comoros; Ylang Ylang Extra; Ylang Ylang I; Ylang Ylang II; Ylang Ylang III; Ylang Ylang, Fine; and Yuzu. etc. Such oil extracts may be used alone or in combination, and/or in combination with approved drugs and/or other agents and compounds of the present invention.

As used herein, "herbal composition" or "natural composition" refers to composition containing one or more herbs.

As used herein, "raw materials" means any part of an herbal spice (for example, but not limited to, roots, leaves, flowers, seeds, stems, stalks, caps, or spores) as well as whole plants that can be used to make the compositions disclosed herein. In one embodiment, any of about 5, 6, 7, 8, 9, 10, 11, 12, 13, 14, 15, 16, 17, 18, 19, 20, 25, 30, 35, 40, 45, 50, 55, 60, 65, 70, 80, 90, 100, 200, 300, 400, 500, 600, 700, 800, 900, 1000, 2000, 3000, 4000, 5000, 6000, 7000, 8000, 9000, or 10000 g or more of raw materials, inclusive, including any value in between these numbers can be used to make the compositions disclosed herein.

As used herein, "water-soluble" or similar is defined as the ability of the herbal composition to remain in clear solution form without precipitation or separation of the particles for a minimum period of 24 hours and the ability of the herbal composition to result into a clear and transparent solution, without precipitation or separation of particles for a minimum period of 15 minutes when added to water m ratio of 1:200 and above.

As used herein, "pH buffer" is defined as a mixture of a weak acid and its conjugate base or a weak base and its conjugate acid.

As used herein, "pharmaceutically acceptable excipient" is defined as substances other than the active pharmaceutical ingredient (AIT) that have been appropriately evaluated for safety and are intentionally included in a drug delivery system which facilitate processing of the drug formulation during its manufacture; protect, support, and/or enhance stability, bioavailability, or patient acceptability; facilitate in the effectiveness and/or delivery of the drug formulation and assist in maintaining the integrity of the drug formulation during its storage across its shelf life. pharmaceutically acceptable excipients but not limited to adsorbent, diluent, filler, sweetener, flavoring agent, polymers, carrier, gelling agent, stabilizer, surfactant, plasticizer, lubricant, reducing agent, buffer agent, sweetening agent, base, corrigent, binder, suspending agent, antioxidant, polish, coating, wetting agent, gelling agent, wet modifier, filler, antifoaming agent, refrigerate agent, coloring matter, flavoring agent, perfume, sugar coating agent, isochronizing agent, softener, emulsifying agent, foaming agent, pH modifier, anti-frothing agent, flavoring agents, preservatives, diluent, excipient, dispersing agent, disintegrator, fragrance, desiccant, antiseptics, preservative, solubilizing agent, solubilizer, solvent, superplasticizer, antistatic agent, extender, moisturizing agent, and the like.

As used herein, "pharmaceutical composition" or similar refers to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration.

In one preferred embodiment the composition takes the form of solution, liquid, gel, suspension, emulsion, lotion, tablet, pill, pellet, capsule, powder, sustained-release formulation, suppository, emulsion, aerosol, spray, drop, nanoemulsion, buccal or sublingual form, a transdermal patch or other form suitable for use, such as cosmetic cream, body lotion, body milk, ointment or shampoo.

The present compositions, manufacture, products, processes, methods, and/or methods of use, prevention and treatment therefore, can take the form of solutions, liquids (e.g. WO2010106191), gels (e.g. WO2007126915), suspensions, emulsion, tablets, pills, pellets, capsules, capsules containing liquids (e.g. WO2010106191), powders (US20040162273), sustained-release suppositories, emulsions, aerosols, sprays (e.g. WO/2010/109482), drops, suspensions, nanoemulsions (e.g. WO2010070675), sublingual compositions (e.g. WO2009067536), a transdermal patch (e.g. U.S. Pat. Nos. 5,004,610; 5,342,623; 5,344,656; 5,364,630; 5,462,745; and 5,508,038; 5,077,104; 5,268,209; 4,908,027; 5,633,008; 4,839,174; 4,943,435; and 5,167,242) or any other form suitable for use.

Pharmaceutical compositions containing the at least one agent, compound, or drug of the present invention may be prepared in any form, such as oral dosage form (powder, tablet, capsule, soft capsule, aqueous medicine (e.g. U.S. Pat. No. 6,068,850), syrup, elixirs pill, powder, sachet, granule), or topical preparation (cream, ointment, lotion, gel, emulgel (e.g. WO2007129162), balm, patch, paste, spray solution, aerosol and the like), or injectable preparation (solution, suspension, emulsion).

As used herein, "particle" is defined as a minute portion of a substance which when having a size range between 1 and 100 nanometers are called as ultrafine and/or nano particles and having size range between 100 and 2500 nanometers are termed as fine particles.

As used herein, "emulsifier" is defined as an emulsifying agent compound or substance that acts as a stabilizer for emulsions. An emulsion is a mixture of two or more liquids that are normally immiscible. The emulsifier prevents immiscible liquids from separating from each other in the mixture. Emulsifier may also be defined as a type of surfactant. In an embodiment, emulsifier are selected but not limited to group comprising polyoxyethylene products of hydrogenated vegetable oils such as commercially available Dal da, Margarine, polyethoxylated castor oils, poly ethoxy lated hydrogenated castor oil, polyoxyethylene-sorbitan-fatty acid esters, polyoxyethylene castor oil derivatives or a combination thereof, commercially available as Kolhphor®, such as Kolliphor® EL (PEG-35 castor oil), Kolhphor® RH40 (PEG-40 hydrogenated castor oil), Kolliphor® RH60 (PEG-60 hydrogenated castor oil), Labrasol® (PEG-8 Capryiic/Capric Glycerides), Gelucire® (Stearoyl polyoxylglycerides), Polysorbates, PLURONIC® L-64 and L-127 (block copolymers based on ethylene oxide and propylene oxide), TRITON™ X 100 (Polyethylene glycol tert-octylphenyl ether), SIMULSOL™ (polyoxy ethylated products comprising Polyoxy ethylated lauric alcohol, Polyoxyethylated cetostearyl alcohol, Polyoxyethylated stearic acid and like), NIKKOL™ HCO-50 (Polyoxyethylene (50) hydrogenated castor oil), NIKKOL™ HCO-35 (Polyoxyethylene (35) hydrogenated castor oil), NIKKOL™ HCO-40 (Polyoxyethylene (40) hydrogenated castor oil), NIKKOL™ HCO-60 (Polyoxyethylene (60) hydrogenated castor oil), TWEENS® (Polysorbates) and/or their mixture thereof.

As used herein, "lipophilic solvent" is defined as a lipid loving solvent. A lipophilic solvent are selected from, but not limited to fractionated oil, Caprylic triglyceride, Capne triglyceride and/or an oil containing medium chain fatty acid triglycerides that herein is defined as triglycerides with two or three fatty acids having an aliphatic chain of 8 to 12 carbon atoms, CAPTEX 300, isopropyl myristate, isopropyl palmitate, ethyl linoleate, Ethyl oleate esters of fatty acids, propylene glycol dicaprylate, propylene glycol dilaurate or oils containing propylene glycol di fatty acid esters and/or their mixtures thereof.

As used herein, "dose dependent cytotoxicity" refers to increase in cytotoxicity with increase concentration of the compound.

As used herein, "soluble proteins" means proteins with polar charge on them that can dissolve in water as water is also a polar compound.

As used herein, "disease" refers to an abnormal condition that negatively affects the structure or function of all or part of an organism, and that is not immediately due to any external injury. In an embodiment, the disease is cancer. In some embodiments, the disease may be a localized or non-localized. In an embodiment, disease includes for example but not limited to, a muscular dysfunction, a neoplastic disorder, a dermal disease such as atopy, a respiratory disease, such as rhinitis, sinusitis, nasopharyngeal cancer, bronchitis, asthma, chronic obstructive pulmonary disease, bronchiectasis, pneumonia, and lung cancer, a digestive disease such as stomatitis, oral cavity cancer, esophagitis, esophageal cancer, gastritis, stomach cancer, inflammatory bowel disease, and colorectal cancer, and a genital disease such as vaginitis, cervicitis, and uterine cervical cancer. In some other embodiments, the disease may be a systemic disease including, but not limited to, a vascular disease such as sepsis, thrombosis/embolism, arteriosclerosis, stroke, acute coronary syndrome, and ischemic vascular disease, a metabolic disease such as diabetes and obesity, a pulmonary disease such as emphysema, and acute respiratory distress syndrome, a bone disease such as arthritis and osteoporosis, and a cranial nerve disease such as dementia, neurodegenerative diseases, and depression. In an embodiment, the disease is a blockade of a communication process between a first cell and a second cell, wherein the first cell elaborates a first extracellular vesicle containing a component of a mitophagy pathway and/or autophagy pathway and the first extracellular vesicle is taken up by the second cell. In another embodiment, the component belongs to a fission pathway of mitophagy. In yet another embodiment, the method is a therapeutic method to treat a disease.

Cancers (or cancer cells) discussed herein can be any type of cancer, such as a carcinoma, sarcoma, lymphoma, leukemia, melanoma, mesothelioma, multiple myeloma, or seminoma. Cancer can be metastatic cancer. Cancer cells can be derived from solid or non-solid tumors. Cancer can be a recurrent cancer, such as recurrent liver cancer following liver transplant therapy. Cancers and cancer cell types contemplated herein include, but are not limited to: adrenal cancer, anal cancer, bladder cancer, blood cancer, bone cancer, brain cancer, breast cancer, cervical cancer, chronic or acute leukemia, CNS cancer, colon cancer, cutaneous or intraocular melanoma, endocrine cancer, endometrial carcinoma, esophageal cancer, fallopian tube carcinoma, follicular lymphoma and other non-Hodgkin's lymphomas, head or neck cancer, Hodgkin's disease, kidney cancer, larynx cancer, large intestinal cancer, liver cancer, lung cancer, lymphocytic lymphoma, ovarian cancer, pancreatic cancer, parathyroid cancer, penile cancer, pituitary adenoma, primary CNS lymphoma, prostate cancer, rectal cancer, renal cell carcinoma, renal pelvic cancer, skin cancer, small cell lung cancer, small intestinal cancer, soft tissue tumor, spleen cancer, stomach cancer, testicular cancer, thyroid cancer, ureter cancer, urethral cancer, uterine cancer, vaginal cancer, and vulval cancer, or a combination thereof. In some embodiments, as described in more detail below, the cancer cells are pancreatic cancer, hepatic (liver) cancer, breast cancer, or cervical cancer.

As used herein, "extraction yield" or similar is calculated as:

Yield (%)=(weight of solvent free extract (g)/Dry extract weight)*100

As used herein, "half-life stability" refers to a time when the pharmacological property of the compound reduces to half of its initial value.

As used herein, "a functional health food" refers to food providing enhanced physical; psychological, physiological, or other functionality by adding the compositions, agent(s), compound(s), drug(s), analogs, derivatives, or compositions of the present invention to conventional food for the benefit of a human or mammal.

Embodiments

In an embodiment, the compositions or herbal composition, of the present invention comprise at least one extract selected from the group comprising Tulsi, turmeric, piperine, green tea, ginger, ashwagandha, garlic, Tulsi, wheatgrass.

In an embodiment, extract refers to a pure extract.

In an embodiment, extract refers to crude extract.

In an embodiment, the composition or herbal spice is not an extract but particles of one or more herbal spice.

In some embodiment, the composition contains at least two extracts selected from Tulsi, turmeric, piperine, green tea, ginger, ashwagandha, garlic, Tulsi, wheatgrassm, such as but not limited to Tulsi and turmeric, piperine and ashwangandha, garlic and ashwagandha and so on. In some embodiments, the compositions combine two extracts in a ratio of about 1:1, to about 1:2, to about 1:5, to about 1:10, to about 1:50, to about 1:100, to about 1:500, to about 1:1000.

In some embodiment, the composition contains three extracts selected from Tulsi, turmeric, piperine, green tea, ginger, ashwagandha, garlic, Tulsi, wheatgrass. In some embodiments, the compositions combine three extracts in a ratio of about 1:1:1, to about 1:2:1, 1:3:1, 1:4:1, 1:5:1, 1:10:1, 2:1:1, 3:1:1, 4:1:1 or 5:1:1 respectively.

In some embodiment, the composition contains at least four extracts selected from Tulsi, turmeric, piperine, green tea, ginger, ashwagandha, garlic, Tulsi, wheatgrass. In some embodiments, the compositions combine three extracts in a ratio of about 1:1:1:1, to about 1:2:1:1, 1:3:1:1, 1:4:1:1, 1:5:1:1, 1:10:1:1, 1:2:2:1, 1:2:3:1, 1:2:4:1, 1:2:5:1, 1:2:10:1, 2:1:1:3, 3:1:1:6, 4:1:1:7 or 5:1:1:8.

In some embodiment, the composition contains at least five extracts selected from Tulsi, turmeric, piperine, green tea, ginger, ashwagandha, garlic, Tulsi, wheatgrass. In an embodiment, the composition may in a ratio of about 1:1:1:1:1, to about 1:2:1:1:2, 1:3:1:1:2, 1:4:1:1:2, 1:5:1:1:2, 1:10:1:1:2, 1:2:2:1:2, 1:2:3:1:2, 1:2:4:1:2, 1:2:5:1:2:2, 1:2:10:1:2, 2:1:1:3:2, 3:1:1:6:2, 4:1:1:7:2 or 5:1:1:8:2; 1:2:1:1:1.

In some embodiment, the composition contains at least six extracts selected from Tulsi, turmeric, piperine, green tea, ginger, ashwagandha, garlic, Tulsi, wheatgrass. In an embodiment, the composition may in a ratio of about 1:1:1:1:1:1, to about 1:1:1:1:1:2, 1:2:1:1:2:1, 1:3:1:1:2:1, 1:4:1:1:2:1, 1:5:1:1:2:1, 1:10:1:1:2:1, 1:2:2:1:2:1, 1:2:3:1:2:1, 1:2:4:1:2:1, 1:2:5:1:2:2:1, 1:2:10:1:2:1, 2:1:1:3:2:1, 3:1:1:6:2:1, 4:1:1:7:2:1 or 5:1:1:8:2:1; 1:2:1:1:1:1.

In some embodiments, the composition contains at least seven extracts selected from Tulsi, turmeric, piperine, green tea, ginger, ashwagandha, garlic, Tulsi, wheatgrass. In an embodiment, the composition may in a ratio of about 1:1:1:1:1:1:1, to about 1:2:1:1:2:1:1, 1:3:1:1:2:1:1, 1:4:1:1:2:1:1, 1:5:1:1:2:1:1, 1:10:1:1:2:1:1, 1:2:2:1:2:1:1, 1:2:3:1:2:1:1, 1:2:4:1:2:1:1, 1:2:5:1:2:2:1, 1:2:1:1:2:1:1, 2:1:1:3:2:1:1, 3:1:1:6:2:1:1, 4:1:1:7:2:1:1 or 5:1:1:8:2:1:1; 1:2:1:1:1:1:1.

In some embodiment, the composition contains Tulsi, turmeric, piperine, green tea, ginger, ashwagandha, garlic, Tulsi, wheatgrass. In an embodiment, the composition may in a ratio of about 1:1:1:1:1:1:1:1:1, to about 1:2:1:1:2:1:1:1, 1:3:1:1:2:1:1:1:1, 1:4:1:1:2:1:1:1:1, 1:5:1:1:2:1:1:1:1, 1:10:1:1:2:1:1:1:1, 1:2:2:1:2:1:1:1:1, 1:2:3:1:2:1:1:1:1, 1:2:4:1:2:1:1:1:1, 1:2:5:1:2:2:1:1:1:1, 1:2:10:1:2:1:1:1:1, 2:1:1:3:2:1:1:1:1, 3:1:1:6:2:1:1:1:1, 4:1:1:7:1:1:1:1 or 5:1:1:8:2:1:1:1:1; 1:2:1:1:1:1:1:1:1.

In an embodiment, the composition contains herbal spices selected from Tulsi, turmeric, piperine, green tea, ginger, ashwagandha, garlic, Tulsi, wheatgrass, along with a drug to treat concerned disease.

In some embodiments, said extracts could be diluted at about 1:10 to about 1:100 to about 1:1000 to about 1:100 to about 1:10,000.

In an embodiment, the extract according to the present invention is produced by $CO_2$ extraction, DMSO extraction, combination of $CO_2$ extraction and DMSO extraction, cold-press extraction and steam distillation extraction. Methods for producing extracts (e.g. natural oils, absolutes, and concretes, etc.) are well known to the art (e.g. Harborne, 1998. Phytochemical Methods A Guide to Modern Techniques of Plant Analysis; I. Walinga, J. J. van der Lee, V. J. G. Houba, W. van Vark, I. Novozamsky, 1995, Plant Analysis Manual; Elizabeth M. Williamson, David T. Okpako, Fred J. Evans, 1996, Selection, Preparation and Pharmacological Evaluation of Plant Material; U.S. Pat. No. 6,241,975 BI; Schnaubelt, K. (2002). Biology of Essential Oils. San Rafael, CA: Terra Linda Scent; Guenther, E. (1982). The Essential Oils. Melbourne, Fl: Krieger Publishing; Food and Agriculture Organization of the United Nations (1995). Basic Principles of Steam Distillation. Retrieved Aug. 18, 2005, from http://www.fao.org/docrep/V5350c/V5350cl3.htm; Catty, S. (2001). Hydrosols: The Next Aromatherapy. Rochester, VT: Healing Arts Press; Burnett, C. (2014) Safety Assessment of Citrus-Derived Peel Oils as Used in Cosmetics, Cosmetic Ingredient Review, Personal Care Products Council; NTP. (2000), Lemon Oil, Lime Oil, National Toxicology Program, U.S. Department of Health & Human Services; Guba, R. (2002); The Modern Alchemy of Carbon Dioxide Extraction. International Journal of Aromatherapy 12 (3), 120-126; http://www.cdenbotanicals.com/extraction-methods, CN102391911: Supercritical extraction method for orange peel essential oil; Parameters optimization of supercritical fluid-$CO_2$ extracts of frankincense using response surface methodology and its pharmacodynamics effects."/Jing Zhou, Xing-miao Ma, Bi-Han Qiu, Jun-xia Chen, Lin Bian, Lin-mei Pan/Journal of Separation Science, Volume 36, Issue 2, January 2013, Pages 383-390) incorporated herein in their entireties. Sources of orange, frankincense and cannabis (natural) oils and extracts In an embodiment, steam distillation could be used for extracting natural oil from plants, however there are many other methods suitable for obtaining and concentrate the aromatic constituents of plant materials.

In an embodiment, the extraction yield is about 70% 80%, 85%, 90%, 95%, 99% or more.

Anti-Cancer Effects

The present composition can induce the apoptosis of the cancer cell in a subject accordance with this invention. The cancer cells include abnormal cancer cells associated with lymphoma, leukemia, plasma cell dyscrasias, multiple myeloma, amylodosis, also as known as hepatocellular cancer, colorectal cancer, renal cancer, breast cancer, prostate cancer, stomach cancer, lung cancer, nasal-pharyngeal cancer, ovarian cancer, bone cancer, gastric cancer, pancreatic cancer, and melanoma.

Cytotoxicity is the quality of being toxic to cells. In an embodiment, the composition is cytotoxic to a cancer cell. There are certain transcription factors that regulate the expression of inflammatory gene products and are constitutively active in many cancers. Chronic inflammation results from conditions like pancreatitis, prostatitis and hepatitis. It leads to cell proliferation, survival, invasion, angiogenesis, metastasis and resistance to chemotherapy and radiation.

In an embodiment, eugenol found abundantly in Tulsi leaves demonstrates anticancer effects by causing cell death, cell cycle arrest, inhibiting migration, metastasis and angiogenesis across various cancer types. It considers specific molecular targets and kills the cancer cell. Eugenol has antioxidant properties and it combats oxidative stress by scavenging free radicals. In an embodiment, compounds in garlic, pepper, rosemary, turmeric, and cinnamon appear to influence phase I and phase II enzymes. Garlic has bioactive compounds and demonstrate preventative effects against breast cancer at many stages like initiation, promotion and progression. Their compounds affect cell signaling and the pathways the cancer cell takes which affects their growth and reduces it. Turmeric decreases expression of RTKs. Curcumin interferes with the cell signaling pathway of cancer and acts on the proliferation of cancer cells. It shows the effects of anti-invasive activities to regulate the cancer cell and recently curcumins' ability to modulate the expression of some nucleotides in breast cancer. Green tea catechins have antioxidant properties and can neutralize reactive oxygen species. Catechins can detect copper which is commonly found in cancer cells which helps them detect the cancer cells and inhibit their growth. Piperine can also modify the activities of enzymes and transcription to help reduce cancer in the body. Piperine included the apoptosis of cancer cells, cell proliferation, cell cycle arrest, and modulations and detoxification. Piperine also alters the redox homeostasis in a cell and tissue-specific way to retard cancer development. Piperine influences signaling and induces apoptosis in UV-irradiated skin cells; it has chemopreventive potential. Piperine also inhibits glycoprotein activity as it enhances the apoptosis in cancer cells and also enhances the radiosensitization of otherwise resistant tumors and it doesn't affect the beneficial chemicals of fruits and vegetables. Ashwagandha can be used in two ways to help reduce the risk of cancer. First it is in combination with radio and chemotherapy or secondly used as an adjunct therapy as it is very safe.

In an embodiment, IC50 of the composition is about 10 μg/ml. In another embodiment, IC50 value of the composition is about 20 μg/ml, 25 μg/ml, 30 μg/ml, 50 μg/ml, 75 μg/ml or 100 μg/ml. In another embodiment, IC50 of the composition is about 5 μg/ml, 7 μg/ml, 10 μg/ml.

In an embodiment, the composition provides dose dependent toxicity. In another embodiment, the composition is dose independent toxicity.

In an embodiment, the composition is treat a disease such as but not limited to cancer. Examples of cancer related diseases and conditions include prostate cancer, breast cancer, lung cancer, colorectal cancer, bladder cancer, uterine cancer, ovarian cancer, lymphoma, skin cancer, stomach cancer, liver cancer, wasting diseases, and other cancers.

In an embodiment, the composition has inhibition percentage of about 50%, 60%, 70%, 80%, 90% or more on a cancer cell line using MTT assay at a concentration of about 5 μM, 10 μM, 20 μM, 50 μM, 100 μM, 1000 μM or more.

In an embodiment, composition can be administered in an adjuvant setting or administered in a neoadjuvant setting.

"Adjuvant setting" refers to a clinical setting in which an individual has had a history of a proliferative disease, particularly cancer, and generally (but not necessarily) has been responsive to therapy, which includes, but is not limited to, surgery, radiotherapy, and chemotherapy. However, because of a history of the proliferative disease (such as cancer), these individuals are considered at risk of developing that disease. Treatment or administration in the "adjuvant setting" refers to a subsequent mode of treatment.

The methods provided herein may also be practiced in a "neoadjuvant setting," that is, the method may be carried out before the primary/definitive therapy. In some aspects, the individual has previously been treated. In other aspects, the individual has not previously been treated. In some aspects, the treatment is a first line therapy.

In some aspects, any of the methods of treatment described herein can further comprise administering one or more additional anti-cancer therapies along with herbal composition to the individual. Various classes of anti-cancer agents can be used along with herbal composition. Non-limiting examples include alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antincoplastics.

Formulation Using Herbal Composition

In an embodiment, herbal composition could be in the form of powder, liquid, gel (semi-solid), etc. In another embodiment, the herbal composition is provided as a powder or liquid suitable for the consumer to add to the food or beverage. For example, in some embodiments, the herbal composition may be used in the form of a powder, for example mixed with a beverage or stirred with a semi-solid food such as pudding, topping, sauce, puree, cooked cercal or salad dressing Or may be administered to an individual by being added to the food in a sealed form in the cap of a food or beverage container to be released, for example, just before consumption.

In an embodiment, herbal composition may be administered as a pharmaceutical composition where the herbal composition is mixed with suitable carriers or excipient. In treating a patient exhibiting a disorder of interest, a therapeutically effective amount of the herbal composition is administered.

When the herbal composition is administered without combination with any other substances, the composition may be encased in a suitable capsule, such as a gelatin capsule. When administered in admixture with other excipients, adjuvants, binders, diluents, disintegrants, etc., the herbal composition may be compressed into a capsule or caplet in a conventional manner that is well-known in the art.

In some embodiments, the composition contains pharmaceutical carriers (vehicles), or excipients known to the art. Examples include water-soluble organic solvents, non-ionic surfactants, water-insoluble lipids, organic liquids/semi-solids, cyclodextrins and phospholipids. They may also include gelatin, lactic acid, stearic acid or salts or complexes thereof, starch, milk, sugar, certain types of clay, including magnesium or calcium stearate, talc, oils, gums, vegetable fats, lipids, or and glycols. Examples of suitable pharmaceutical vehicles are also described in Remington's Pharmaceutical Sciences, Alfonso R. Gennaro cd., Mack Publishing Co. Easton, Pa., 19th ed., 1995, pp. 1447 to 1676, incorporated herein by reference.

Addition of other materials to the compositions described herein can be desirable. Other inactive material or combination of materials that are suitable for administration, "excipients", can be added to the compositions described herein. Frequently, excipients serve to improve the features of the therapeutic agent composition, e.g., by providing more efficient and reproducible delivery of the therapeutic agent, improving the handling characteristics of powders (e.g., flowability and consistency), the stability of the agent, and/or facilitating manufacturing and filling of dosage forms. In particular, excipient materials may function to further improve the physical and chemical stability of the therapeutic agent, and enhance uptake of the therapeutic agent into body, thus increasing efficacy of the therapeutic agent. Excipients may further serve to minimize the residual moisture content and/or hinder moisture uptake, minimize particle aggregation, or modify particle surface properties (i.e., rugosity) of the compositions. An excipient may also serve as a bulking agent when it is desired to reduce the concentration of therapeutic agent in the formulation. Furthermore, an excipient may server as a masking agent for objectionable smells and/or tastes.

In some embodiments of the invention, a water-absorbing and gel-forming material is added to the composition to improve drug absorption. Typically, this gel-forming material is used as a carrier, either alone or in combination with a water-absorbing, but non-gel-forming substance. Exemplary, gel-forming materials include, for example, cellulose derivatives such as hydroxypropyl cellulose, hydroxypropyl methyl cellulose, methyl cellulose, hydroxy ethyl cellulose, and carboxymethyl cellulose sodium.

In an embodiment, oral solid dosage form unit dosage forms of the present invention can be used for sending the pharmaceutically active agents of any expectation. As used herein, "effective dose" refers to patient's the biological response of expectation or the amount of the medicine of medical response or medicament of producing. According to the present invention, effective dose can change according to the medicament of administration and the desired patient's of doctor biological response or medical response. Generally speaking, can use conventionally the amount with the pharmaceutically active agents of other unit dosage forms administration, and by unit dosage forms of the present invention by its administration. Can be in view of carry out the dosage of regulating drug activating agent because of the different absorption difference that cause of route of administration. As used herein, the most medicament that term "selectivity" represents institute's administration is by oral mucosa but not pass through gastrointestinal tract.

Half-life stability is defined as time taken for concentration of a biological substance (such as a medication) to decrease from its maximum concentration (Cmax) to half of Cmax.

In an embodiment, half-life stability of the composition is about 1 year, 2 years, 3 years, 4 years, 5 years, 6 years, 7 years, 8 years, 10 years at room temperature (about 25° C.).

In an embodiment, the composition is in form of a nanoparticle as described in US20210196829A1, U.S. Ser. No. 10/738,268B2 incorporated by reference in its entirety.

In an embodiment, the composition is water soluble as described in U.S. Ser. No. 11/351,117B2.

Method of Forming Composition

In some aspects, raw materials from herbal spice can be used to manufacture the compositions described herein. The extracts can be obtained by extracting raw materials from different herbal spice together or individually. Following extraction, the individually extracted material from a herb can be combined. In one embodiment, a liquid extract can be filtered away from the remaining solid material prior to being concentrated or, in the case of individual extractions, prior to being combined. In other embodiments, the remaining solid material can undergo further extraction. In some embodiments, the extracts can be concentrated or, alternatively, the extracts can be left in their raw unconcentrated form.

Example 1

Cytotoxicity Assay: Doxorubicin (a drug used in chemotherapy) showed that as the concentration of doxorubicin increased, the cytotoxicity also increased (from 11.7% at 0.1 μM to 69.2% at 50 μM). The IC50 value is 9.391 μM, which is the concentration of doxorubicin that causes 50% cytotoxicity.

In an embodiment, compounds Wheat Grass, Ginger, Tulsi, Garlic, Ashwagandha, Green Tea, Piperine, Turmeric were observed that as the concentration of the substance increased, the % cytotoxicity increased. The IC50 value is the concentration at which 50% cytotoxicity is observed for each substance. Some substances, such as Wheat Grass, Ginger, and Tulsi, have IC50 values greater than 100 μg/ml, indicating that higher concentrations are required to reach 50% cytotoxicity. The substances Garlic, Ashwagandha, Green Tea, Piperine, and Turmeric have IC50 values less than 100 μg/ml, suggesting relatively lower concentrations are needed to induce 50% cytotoxicity.

Table 1 provides cytotoxicity assay of herbal compounds.

TABLE 1

Cytotoxicity assay of herbal compounds.

| Sample | | OD1 | OD2 | OD3 | Average OD | % cytotoxicity | IC50 |
|---|---|---|---|---|---|---|---|
| Untreated | | 0.444 | 0.466 | 0.494 | 0.468 | 0.0 | |
| Doxorubicin | 0.1 | 0.429 | 0.463 | 0.348 | 0.413 | 11.7 | 9.391 μM |
| (μM) | 1 | 0.411 | 0.47 | 0.252 | 0.378 | 19.3 | |
| | 10 | 0.234 | 0.26 | 0.194 | 0.229 | 51.0 | |
| | 25 | 0.151 | 0.143 | 0.181 | 0.158 | 66.2 | |
| | 50 | 0.142 | 0.127 | 0.163 | 0.144 | 69.2 | |
| Wheat Grass | 0.01 | 0.378 | 0.379 | 0.37 | 0.376 | 19.7 | >100 μg/ml |
| (μg/ml) | 0.1 | 0.406 | 0.341 | 0.382 | 0.376 | 19.6 | |
| | 1 | 0.433 | 0.403 | 0.295 | 0.354 | 24.4 | |
| | 10 | 0.388 | 0.341 | 0.332 | 0.344 | 26.6 | |
| | 50 | 0.408 | 0.327 | 0.296 | 0.366 | 21.9 | |
| | 100 | 0.384 | 0.347 | 0.366 | 0.377 | 19.4 | |
| Ginger (μg/ml) | 0.01 | 0.378 | 0.345 | 0.32 | 0.348 | 25.7 | >100 μg/ml |
| | 0.1 | 0.324 | 0.347 | 0.284 | 0.318 | 32.0 | |
| | 1 | 0.267 | 0.297 | 0.297 | 0.287 | 38.7 | |
| | 10 | 0.256 | 0.282 | 0.27 | 0.269 | 42.5 | |
| | 50 | 0.263 | 0.261 | 0.302 | 0.275 | 41.2 | |
| | 100 | 0.270 | 0.270 | 0.228 | 0.256 | 45.3 | |
| Tulsi (μg/ml) | 0.01 | 0.354 | 0.374 | 0.402 | 0.377 | 19.5 | >100 μg/ml |
| | 0.1 | 0.318 | 0.328 | 0.383 | 0.343 | 26.7 | |
| | 1 | 0.288 | 0.325 | 0.315 | 0.309 | 33.9 | |
| | 10 | 0.269 | 0.261 | 0.311 | 0.280 | 40.1 | |
| | 50 | 0.263 | 0.299 | 0.255 | 0.272 | 41.8 | |

TABLE 1-continued

Cytotoxicity assay of herbal compounds.

| Sample | | OD1 | OD2 | OD3 | Average OD | % cytotoxicity | IC50 |
|---|---|---|---|---|---|---|---|
| | 100 | 0.247 | 0.285 | 0.237 | 0.256 | 45.2 | |
| Garlic (μg/ml) | 0.01 | 0.348 | 0.362 | 0.364 | 0.358 | 23.5 | >100 μg/ml |
| | 0.1 | 0.347 | 0.408 | 0.382 | 0.379 | 19.0 | |
| | 1 | 0.308 | 0.332 | 0.409 | 0.350 | 25.3 | |
| | 10 | 0.321 | 0.349 | 0.398 | 0.356 | 23.9 | |
| | 50 | 0.294 | 0.308 | 0.361 | 0.321 | 31.4 | |
| | 100 | 0.26 | 0.322 | 0.356 | 0.313 | 33.2 | |
| Ashwagandha (μg/ml) | 0.01 | 0.407 | 0.4 | 0.381 | 0.396 | 15.4 | >100 μg/ml |
| | 0.1 | 0.394 | 0.362 | 0.289 | 0.348 | 25.6 | |
| | 1 | 0.367 | 0.29 | 0.297 | 0.318 | 32.1 | |
| | 10 | 0.381 | 0.301 | 0.265 | 0.316 | 32.5 | |
| | 50 | 0.394 | 0.279 | 0.245 | 0.306 | 34.6 | |
| | 100 | 0.328 | 0.296 | 0.218 | 0.281 | 40.0 | |
| Green Tea (μg/ml) | 0.01 | 0.375 | 0.349 | 0.342 | 0.355 | 24.1 | 5.743 μg/ml |
| | 0.1 | 0.344 | 0.315 | 0.331 | 0.330 | 29.5 | |
| | 1 | 0.272 | 0.284 | 0.334 | 0.297 | 36.6 | |
| | 10 | 0.241 | 0.233 | 0.262 | 0.245 | 47.6 | |
| | 50 | 0.16 | 0.157 | 0.17 | 0.162 | 65.3 | |
| | 100 | 0.14 | 0.158 | 0.148 | 0.149 | 68.2 | |
| Piperine (μg/ml) | 0.001 | 0.307 | 0.372 | 0.332 | 0.337 | 28.0 | 1.561 μg/ml |
| | 0.01 | 0.288 | 0.349 | 0.355 | 0.331 | 29.3 | |
| | 0.1 | 0.264 | 0.276 | 0.262 | 0.267 | 42.9 | |
| | 1 | 0.265 | 0.268 | 0.25 | 0.261 | 44.2 | |
| | 10 | 0.203 | 0.174 | 0.215 | 0.197 | 57.8 | |
| | 25 | 0.166 | 0.182 | 0.195 | 0.181 | 61.3 | |
| Turmeric (μg/ml) | 0.001 | 0.342 | 0.553 | 0.424 | 0.440 | 6.1 | 3.241 μg/ml |
| | 0.01 | 0.339 | | 0.504 | 0.422 | 9.9 | |
| | 0.1 | 0.27 | 0.4 | 0.406 | 0.359 | 23.4 | |
| | 1 | 0.284 | 0.334 | 0.365 | 0.328 | 30.0 | |
| | 10 | 0.187 | 0.181 | 0.108 | 0.159 | 66.1 | |
| | 25 | 0.16 | 0.136 | 0.13 | 0.142 | 69.7 | |

Example 2

Evaluation of in-vitro cytotoxic potential of herbal products in human Lung cancer cell line (A549) by antioxidant assay: All the spices that were used from ginger to turmeric showed a good amount of percentage inhibition for the cancer cells. Some spices, such as garlic, green tea extract, and wheatgrass extract, demonstrate relatively higher cytotoxicity, with percent inhibition reaching as high as 85% or more at certain concentrations. These substances may have potential as cytotoxic agents for further investigation.

In an embodiment, because of the efficacy of each of the spices used, it is quite evident that spices show anti-inflammatory effects. We believe that spices may play a crucial role in suppressing inflammation and preventing and treating cancer and other chronic diseases. The lower cancer incidence in countries with regular spice consumption supports the potential anti-cancer properties of these dietary components. We predict relevant concentrations can not only reduce the spread of cancer but also can have a major control on the occurrence of chronic disorders.

In an embodiment, targeting inflammatory pathways may offer opportunities for both the prevention and treatment of cancer and other chronic diseases.

In an embodiment, free radical scavenging activity as per IC50 value: Green teat extract>Turmeric extract>Ginger extract>Tulsi extract>Wheatgrass extract>Ashwagandha extract>Garlic extract>Piperine.

Table 2 provides IC50 value of different herbal components.

TABLE 2

IC50 value of different herbal components.

| Test item | Conc. (μg/ml) | % Inhibition | IC 50 value |
|---|---|---|---|
| Ascorbic Acid | 10 μg/ml | 13 | 37.54 μg/ml |
| | 20 μg/ml | 24 | |
| | 30 μg/ml | 38 | |
| | 40 μg/ml | 51 | |
| | 50 μg/ml | 63 | |
| | 100 μg/ml | 90 | |
| Turmeric extract | 0.001 mg/ml | 5 | 0.1432 mg/ml |
| | 0.01 mg/ml | 29 | |
| | 0.1 mg/ml | 39 | |
| | 1 mg/ml | 75 | |
| | 5 mg/ml | 85 | |
| Ginger extract | 0.001 mg/ml | 15 | 2.164 mg/ml |
| | 0.01 mg/ml | 14 | |
| | 0.1 mg/ml | 19 | |
| | 1 mg/ml | 40 | |
| | 5 mg/ml | 44 | |
| | 10 mg/ml | 79 | |
| | 25 mg/ml | 75 | |
| | 50 mg/ml | 81 | |
| Piperine | 0.001 mg/ml | 10 | 28.32 mg/ml |
| | 0.01 mg/ml | 10 | |
| | 0.1 mg/ml | 12 | |
| | 1 mg/ml | 16 | |
| | 10 mg/ml | 29 | |
| | 25 mg/ml | 39 | |
| | 50 mg/ml | 60 | |
| | 100 mg/ml | 85 | |
| Tulsi extract | 0.001 mg/ml | 9 | 3.180 mg/ml |
| | 0.01 mg/ml | 13 | |
| | 0.1 mg/ml | 12 | |
| | 1 mg/ml | 24 | |
| | 5 mg/ml | 54 | |
| | 10 mg/ml | 81 | |
| | 25 mg/ml | 86 | |
| Garlic extract | 0.001 mg/ml | 6 | 16.09 mg/ml |

TABLE 2-continued

IC50 value of different herbal components.

| Test item | Conc. (μg/ml) | % Inhibition | IC 50 value |
|---|---|---|---|
| | 0.1 mg/ml | 5 | |
| | 1 mg/ml | 5 | |
| | 5 mg/ml | 15 | |
| | 10 mg/ml | 25 | |
| | 25 mg/ml | 74 | |
| | 50 mg/ml | 77 | |
| | 100 mg/ml | 75 | |
| Green tea extract | 0.001 mg/ml | 2 | 0.102 mg/ml |
| | 0.01 mg/ml | 10 | |
| | 0.1 mg/ml | 56 | |
| | 1 mg/ml | 87 | |
| | 5 mg/ml | 83 | |
| | 10 mg/ml | 85 | |
| Wheatgrass extract | 0.1 mg/ml | 6 | 4.449 mg/ml |
| | 1 mg/ml | 15 | |
| | 5 mg/ml | 50 | |
| | 10 mg/ml | 78 | |
| | 25 mg/ml | 83 | |
| Ashwagandha extract | 0.1 mg/ml | 8 | 5.27 mg/ml |
| | 1 mg/ml | 23 | |
| | 5 mg/ml | 41 | |
| | 10 mg/ml | 66 | |
| | 25 mg/ml | 83 | |

Table 3 provides inhibition data of different herbal components.

TABLE 3

Inhibition data of different herbal components

| Test item | Conc. | OD-1 | OD-2 | OD-3 | Mean | % Inhibition |
|---|---|---|---|---|---|---|
| Blank | 0 | 0.591 | 0.598 | 0.596 | 0.595 | 0 |
| Ginger extract | 0.001 | 0.512 | 0.519 | 0.495 | 0.509 | 15 |
| | 0.01 | 0.514 | 0.514 | 0.502 | 0.510 | 14 |
| | 0.1 | 0.48 | 0.488 | 0.483 | 0.484 | 19 |
| | 1 | 0.376 | 0.377 | 0.324 | 0.359 | 40 |
| | 5 | 0.328 | 0.337 | 0.327 | 0.331 | 44 |
| | 10 | 0.154 | 0.074 | 0.153 | 0.127 | 79 |
| | 25 | 0.085 | 0.083 | 0.285 | 0.151 | 75 |
| | 50 | 0.112 | 0.116 | 0.113 | 0.114 | 81 |
| | 100 | 0.12 | 0.14 | 0.12 | 0.127 | 79 |
| Piperine | 0.001 | 0.542 | 0.521 | 0.536 | 0.533 | 10 |
| | 0.01 | 0.542 | 0.524 | 0.537 | 0.534 | 10 |
| | 0.1 | 0.53 | 0.514 | 0.529 | 0.524 | 12 |
| | 1 | 0.504 | 0.489 | 0.498 | 0.497 | 16 |
| | 5 | 0.447 | 0.445 | 0.413 | 0.435 | 27 |
| | 10 | 0.437 | 0.415 | 0.413 | 0.422 | 29 |
| | 25 | 0.37 | 0.358 | 0.358 | 0.362 | 39 |
| | 50 | 0.227 | 0.242 | 0.238 | 0.236 | 60 |
| | 100 | 0.087 | 0.088 | 0.086 | 0.087 | 85 |
| Tulsi extract | 0.001 | 0.536 | 0.549 | 0.542 | 0.542 | 9 |
| | 0.01 | 0.551 | 0.481 | 0.525 | 0.519 | 13 |
| | 0.1 | 0.528 | 0.527 | 0.523 | 0.526 | 12 |
| | 1 | 0.462 | 0.457 | 0.444 | 0.454 | 24 |
| | 5 | 0.25 | 0.29 | 0.29 | 0.277 | 54 |
| | 10 | 0.113 | 0.116 | 0.118 | 0.116 | 81 |
| | 25 | 0.084 | 0.083 | 0.081 | 0.083 | 86 |
| | 50 | 0.161 | 0.158 | 0.158 | 0.159 | 73 |
| | 100 | 0.223 | 0.221 | 0.225 | 0.223 | 63 |
| Garlic extract | 0.001 | 0.556 | 0.554 | 0.574 | 0.561 | 6 |
| | 0.01 | 0.558 | 0.569 | 0.596 | 0.574 | 3 |
| | 0.1 | 0.554 | 0.569 | 0.576 | 0.566 | 5 |
| | 1 | 0.551 | 0.561 | 0.576 | 0.563 | 5 |
| | 5 | 0.493 | 0.521 | 0.506 | 0.507 | 15 |
| | 10 | 0.459 | 0.454 | 0.428 | 0.447 | 25 |
| | 25 | 0.153 | 0.154 | 0.154 | 0.154 | 74 |
| | 50 | 0.136 | 0.135 | 0.135 | 0.135 | 77 |
| | 100 | 0.144 | 0.159 | 0.15 | 0.151 | 75 |
| Green tea extract | 0.001 | 0.591 | 0.598 | 0.56 | 0.583 | 2 |
| | 0.01 | 0.548 | 0.548 | 0.509 | 0.535 | 10 |
| | 0.1 | 0.26 | 0.279 | 0.243 | 0.261 | 56 |
| | 1 | 0.078 | 0.078 | 0.075 | 0.077 | 87 |

TABLE 3-continued

Inhibition data of different herbal components

| Test item | Conc. | OD-1 | OD-2 | OD-3 | Mean | % Inhibition |
|---|---|---|---|---|---|---|
| | 5 | 0.095 | 0.102 | 0.102 | 0.100 | 83 |
| | 10 | 0.087 | 0.086 | 0.094 | 0.089 | 85 |
| | 25 | 0.212 | 0.243 | 0.511 | 0.322 | 46 |
| | 50 | 0.453 | 0.48 | 0.458 | 0.464 | 22 |
| | 100 | 0.951 | 1.008 | 0.984 | 0.981 | −65 |
| Wheatgrass extract | 0.1 | 0.571 | 0.554 | 0.55 | 0.558 | 6 |
| | 1 | 0.518 | 0.491 | 0.511 | 0.507 | 15 |
| | 5 | 0.296 | 0.296 | 0.297 | 0.296 | 50 |
| | 10 | 0.136 | 0.127 | 0.13 | 0.131 | 78 |
| | 25 | 0.106 | 0.099 | 0.102 | 0.102 | 83 |
| | 50 | 0.137 | 0.141 | 0.142 | 0.140 | 76 |
| | 100 | 0.179 | 0.181 | 0.179 | 0.180 | 70 |
| Ashwagandha extract | 0.1 | 0.553 | 0.542 | 0.551 | 0.549 | 8 |
| | 1 | 0.346 | 0.506 | 0.531 | 0.461 | 23 |
| | 5 | 0.352 | 0.348 | 0.361 | 0.354 | 41 |
| | 10 | 0.209 | 0.201 | 0.201 | 0.204 | 66 |
| | 25 | 0.105 | 0.101 | 0.105 | 0.104 | 83 |
| | 50 | 0.116 | 0.123 | 0.124 | 0.121 | 80 |
| | 100 | 0.157 | 0.162 | 0.165 | 0.161 | 73 |
| Ascorbic Acid (μg/ml) | 1 | 0.731 | 0.696 | 0.699 | 0.709 | 2.3 |
| | 10 | 0.659 | 0.624 | 0.605 | 0.629 | 13.2 |
| | 20 | 0.59 | 0.552 | 0.502 | 0.548 | 24.4 |
| | 30 | 0.472 | 0.431 | 0.455 | 0.453 | 37.6 |
| | 40 | 0.388 | 0.337 | 0.345 | 0.357 | 50.8 |
| | 50 | 0.318 | 0.268 | 0.228 | 0.271 | 62.6 |
| | 100 | 0.074 | 0.066 | 0.069 | 0.070 | 90.4 |
| Turmeric extract (mg/ml) | 0.001 | 0.715 | 0.675 | 0.682 | 0.691 | 4.7 |
| | 0.01 | 0.537 | 0.486 | 0.532 | 0.518 | 28.5 |
| | 0.1 | 0.43 | 0.448 | 0.438 | 0.439 | 39.5 |
| | 1 | 0.148 | 0.221 | 0.18 | 0.183 | 74.8 |
| | 5 | 0.148 | 0.085 | 0.086 | 0.106 | 85.3 |

Materials and Methods

Cell Line

Human Lung carcinoma epithelial cell line, A549 cell line was obtained from the National Centre for Cell Sciences (NCCS, Pune). The cell line was cultured in DMEM (Himedia), supplemented with 10% fetal bovine serum (Sigma-Aldrich), 25 U/ml penicillin, and 25 mg/ml streptomycin (Himedia) at 37° ° C. in a water-saturated atmosphere of 95% air and 5% $CO_2$. The experiments were repeated three times and average OD (absorbance values) were taken and plotted

Extraction Method 8 test compounds (Wheatgrass, Ginger, Garlic, Tulsi, Green tea, Ashwagandha, 95% extract of Piperine and Turmeric) were obtained from the formulation department of Dabur Research Foundation, Sahibabad, Ghaziabad, U.P. 201010. 100 mg of the test compounds was weighed and dissolved in DMSO. After that, it was vortexed thoroughly followed by centrifugation. The clear supernatant was then used for further experimentation.

Cell culture Human Lung carcinoma epithelial cell line, A549 cell line was obtained from the National Centre for Cell Sciences (NCCS, Pune). The cell line was cultured in DMEM (Himedia), supplemented with 10% fetal bovine serum (Sigma-Aldrich), 25 U/ml penicillin, and 25 mg/ml streptomycin (Himedia) at 37° C. in a water-saturated atmosphere of 95% air and 5% $CO_2$.

MTT Assay

The effect of DMSO extracts of 8 test compounds (Wheatgrass, Ginger, Garlic, Tulsi, Green tea, Ashwagandha, 95% extract of Piperine and Turmeric) on A549 human lung carcinoma epithelial cell line was observed by MTT (3-(4, 5-dimethylthiazol-2-yl)-2,5-diphenyl tetrazolium bromide) assay. MTT reagent was purchased from Sigma (Darmstadt, Germany). Cells were counted on a hemocytometer and 10,000 cells/well were plated in 96 well plate in 180 μl of complete media (containing 10% of FBS).

Cells were treated with different concentrations (0.01, 0.1, 1, 10, 50, 100 μg/ml) of Wheatgrass, Ginger, Garlic, Tulsi, Green tea & Ashwagandha extracts and at concentrations (0.001, 0.01, 0.1, 1, 10 and 50 μg/ml) of 95% extract of Piperine and Turmeric for 72 hr. After the stipulated time, MTT solution (5 mg/ml) was added to each well and incubated for 3 hr. The purple-colored precipitate of formazan was dissolved in 150 μl of DMSO (Sigma-Aldrich) by proper mixing. The color absorbance of each well was recorded at 570 nm in a Bioteck microplate reader with a reference serving as blank. Then, IC50 values of DMSO extracts of 8 test compounds were calculated.

Morphological study under phase contrast Phase contrast microscopy—A549 cells were treated with different IC50 concentrations of DMSO extracts of 8 test compounds (Wheatgrass, Ginger, Garlic, Tulsi, Green tea, Ashwagandha, 95% extract of Piperine and Turmeric) for 72 hr.

Following incubation, the cells were observed under phase contrast microscope at 20× Magnification. Pictures were acquired with the help of Toup View software.

Statistical analysis MTT Data were analyzed by using Microsoft office Excel Software.

INCORPORATION BY REFERENCE

All references, including granted patents and patent application publications, referred herein are incorporated herein by reference in their entirety.

What is claimed is:

1. A product comprising a formulation comprising particles of a mixture of herbs comprising at least three herbal components selected from piperine, Ginger, Garlic, Tulsi, Wheatgrass, Ashwagandha, turmeric; wherein the particles are coated with an emulsifier and a lipophilic solvent, such that the formulation is water-soluble, wherein the particles are in a size range of about 50 nm to 500 nm, and the weight ratio the herbal components is the same in the formulation.

2. The product of claim 1, wherein the emulsifier is in amount of 30 to 45 w/w %; lipophilic solvent in amount of 5 to 70 w/w % and the particles in amount of about 1 to 20 w/w %.

3. The product of claim 1, wherein pH of the formulation is about 6.5 to 7.5.

4. The product of claim 1, wherein the product has a shelf-life of about 3 years at a room temperature; and the particles do not settle for a period ranging from 1 month to 6 months as seen using a naked eye.

5. The product of claim 1, wherein the formulation has IC50 approximately the same as that of Doxorubicin.

6. The product of claim 1, wherein the formulation comprises a soluble protein comprising turmerin.

7. The product of claim 1, wherein the formulation has IC50 value for cytotoxicity less than or equal to about 10 μg/ml.

8. The product of claim 7, wherein the formulation provides a dose dependent cytotoxicity.

9. The product of claim 7, wherein the formulation is configured to inhibit a cancer comprising lung cancer.

10. The product of claim 7, wherein the formulation is in liquid states.

11. The product of claim 7, wherein the formulation has an inhibition percentage more than 80% and less than 95% as tested on human Lung cancer cell line A549 using MTT assay.

12. The product of claim 7, wherein the formulation is configured to increase an enzyme activity selected from the group consisting of superoxide dismutase and catalase.

13. The product of claim 7, wherein the formulation comprises an excipient.

* * * * *